US008894997B2

(12) United States Patent
Crowe et al.

(10) Patent No.: US 8,894,997 B2
(45) Date of Patent: Nov. 25, 2014

(54) MONOCLONAL ANTIBODIES TO INFLUENZA H1N1 VIRUS USES THEREOF

(75) Inventors: James E. Crowe, Nashville, TN (US); Christopher F. Basler, Hastings on Hudson, NY (US)

(73) Assignees: Vanderbilt University, Nashville, TN (US); Icahn School of Medicine at Mount Sinai, New York, NY (US)

( * ) Notice: Subject to any disclaimer, the term of this patent is extended or adjusted under 35 U.S.C. 154(b) by 136 days.

(21) Appl. No.: 13/318,020

(22) PCT Filed: Apr. 30, 2010

(86) PCT No.: PCT/US2010/033179
§ 371 (c)(1),
(2), (4) Date: Jan. 13, 2012

(87) PCT Pub. No.: WO2010/127252
PCT Pub. Date: Nov. 4, 2010

(65) Prior Publication Data
US 2012/0100142 A1    Apr. 26, 2012

Related U.S. Application Data

(60) Provisional application No. 61/174,415, filed on Apr. 30, 2009.

(51) Int. Cl.
*A61K 39/395* (2006.01)
*A61K 39/42* (2006.01)
*A61K 39/00* (2006.01)
*C12N 15/74* (2006.01)
*C07K 16/00* (2006.01)
*G01N 33/569* (2006.01)
*C07K 16/10* (2006.01)
*A61K 39/145* (2006.01)

(52) U.S. Cl.
CPC ......... *C07K 16/1018* (2013.01); *C07K 2316/96* (2013.01); *G01N 33/56983* (2013.01); *C07K 2317/21* (2013.01); *A61K 2039/505* (2013.01); *C07K 2317/56* (2013.01); *G01N 2333/11* (2013.01); *C07K 2317/34* (2013.01)
USPC .................. 424/130.1; 424/147.1; 424/159.1; 424/178.1; 424/179.1; 424/209.1; 530/388.3; 435/476

(58) Field of Classification Search
CPC ...................... C07K 2317/622; C07K 2317/92; C07K 16/00; C07K 2319/00; C07K 2317/56; C07K 16/46; C07K 16/462; C07K 17/00; C07K 2316/96; C07K 2319/42; C12N 15/8258; G01N 2333/11; G01N 2469/20
See application file for complete search history.

(56) References Cited

U.S. PATENT DOCUMENTS

| 5,684,146 A | 11/1997 | Okuno et al. .............. 536/23.53 |
| 2002/0054882 A1 | 5/2002 | Okuno et al. .............. 524/186.1 |

FOREIGN PATENT DOCUMENTS

| WO | WO 94/21797 | 9/1994 |
| WO | WO 2008/028946 | 3/2008 |

OTHER PUBLICATIONS

Tjelle et al., Monoclonal Antibodies Produced by Muscle after Plasmid Injection and Electroporation, 2004, Molecular Therapy, vol. 9, No. 3, pp. 328-336.*
"Anti-1918 influenza HA immunoglobulin heavy chain variable region [*Homo sapiens*]," NCBI accession No. ABY48865, Sep. 27, 2008.
"Anti-1918 influenza HA immunoglobulin heavy chain variable region [*Homo sapiens*]," NCBI accession No. ACI04579, Sep. 27, 2008.
"Immunoglobulin heavy chain variable region [*Homo sapiens*]," NCBI accession No. ABY48866, Sep. 22, 2008.
"Immunoglobulin light chain variable region [*Homo sapiens*]," NCBI accession No. ABY48868, Sep. 22, 2008.
Ekiert et al., "Antibody recognition of a highly conserved influenza virus epitope," *Science*, 324:246-251, 2009.
Hancock et al., "Cross-reactive antibody responses to the 2009 pandemic H1N1 influenza virus," *N. Engl. J. Med.*, 361:1945, 2009.
International Search Report and Written Opinion issued in PCT/US2010/033179, dated Dec. 31, 2010.
Katz et al., "Serum cross-reactive antibody response to a novel influenza a (H1N1) Virus after vaccination with seasonal influenza vaccine ," *MMWR Morb. Mortal. Wkly Rep.*, 58:521, 2009.
Shibuya et al., "Identification of human monoclonal Fab with neutralizing activity agains H3N2 influencza A strain from a newly constructed human Fab library," *Microbiol. Immunol.*, 52:162-170, 2008.
Sui et al., "Structural and functional bases for broad-spectrum neutralization of avian and human influenza A viruses," *Nat. Struct. Mol. Biol.*, 16:265-273, 2009.
Xing and Cardona, "Preexisting immunity to pandemic (H1N1) 2009," *Emerg. Infect. Dis.*, 15:1847, 2009.
Yoshida et al., "Cross-protective potential of a novel monoclonal antibody directed against antigenic site B of the hemagglutinin of influenza A viruses ," *PLoS Pathog.*, 5:e1000350, 2009.
Yu et al., "An optimized electrofusion-based protocol for generating virus-specific human monoclonal antibodies," *J Immunol Methods*, 336(2):142-151, 2008.
Yu et al., "Neutralizing antibodies derived from the B cells of 1918 influenza pandemic survivors," *Nature*, 455:532-536, 2008.

* cited by examiner

*Primary Examiner* — Benjamin P Blumel
(74) *Attorney, Agent, or Firm* — Parker Highlander PLLC

(57) ABSTRACT

The present invention is directed to particular monoclonal antibodies and fragments thereof that find use in the detection, prevention and treatment of influenza virus infections. In particular, these antibodies may neutralize or limit the replication of H1N1 influenza virus. Also disclosed are improved methods for producing such monoclonal antibodies.

6 Claims, 11 Drawing Sheets

Sa Antigenic Site

```
        128    156      162
         |      |        |
1918    PN    KKGSS    PKLSKS
Sw/30   PN    KKENS    PKLSKS
1943    PK    EKDGS    PNLKNS
1947    PK    ETDGS    PKLSKS
1977    PK    EKNGS    PNLSKS
1999    PN    GKNGL    PNLSKS
```

2B12-induced mutations
(K166OQ, K166E OR K166P)

Sa Antigenic Site

```
        186            198
         |              |
1918    PTGTDQQSLYQNA
Sw/30   PTSTDQQSLYQNA
1943    SSIKEQQTLYQKA
1947    SNIEDQKTLYRKE
1977    SNIEDQKTIYRKE
1999    PNIGNQRALYNTE
```

1F1 and 1I20-induced
mutation (P186B)

FIG. 2

```
Swine_1930      ------MKAILLVLLCAFAATNADTLCIGYHANNSTDTVDTVLEKNVTVTHSVNLLEDSH
SC_1918         ------MEARILVLLCAFAATNADTICIGYHANNSTDTVDTVLEKNVTVTHSVNLLEDSH
1943_HA_Weiss   ------MKARLVLLCALAATDADTICIGYHANNSTDTVDTILEKNVTVTHSVNLLEDSH
USSR_1977       KIKKTKMKAKILVLLCALSATDADTICIGYHANNSTDTVDTVLEKNVTVTHSVNLLEDSH
Mexican_Flu     ------MKAILVVLLYTFATANADTLCIGYHANNSTDTVDTVLEKNVTVTHSVNLLEDKH
                      *:* *:***  ::::::***:************:***************.*

Swine_1930      NGKLCRLGGIAPLQLGKCNIAGWLLGNPECDLLLTVSSWSYIVETSNSDNGTCYPGDFID
SC_1918         NGKLCKLKGIAPLQLGKCNIAGWLLGNPECDLLLTASSWSYIVETSNSENGTCYPGDFID
1943_HA_Weiss   NGKLCRLKGIAPLQLGKCNIAGWILGNPECESLLSERSWSYIVEIPNSENGTCYPGDFTD
USSR_1977       NGKLCRLKGIAPLQLGKCNIAGWILGNPECESLVTKKSWSYIAETPNSENGTCYPGYFAD
Mexican_Flu     NGKLCKLRGVAPLHLGKCNIAGWILGNPECESLSTASSWSYIVETPSSDNGTCYPGDFID
                *****:* *:***:**** ****:******: *  :  ****:*  .:*:******* * *

Swine_1930      YEELREQLSSVSSFEKFEIFPKTSSWPNHETTRGVTAACPYAGASSFYRNLLWLVKKENS
SC_1918         YEELREQLSSVSSFEKFEIFPKTSSWPNHETTKGVTAACSYAGASSFYRNLLWLTKKGSS
1943_HA_Weiss   YEELREQLSSVSSFERFEIFPKESSWPKHNTARGVTAACSHAGKSSFYRNLLWLTEKDGS
USSR_1977       YEELREQLSSVSSFERFEIFPKERSWPKHNVTRGVTASCSHKGKSSFYRNLLWLTEKNGS
Mexican_Flu     YEELREQLSSVSSFERFEIFPKTSSWPNEDSNKGVTAACPHAGAKSFYRNLIWLVKKGNS
                ***************:******: ***:: . :****:*  :  .****.:**:.*  *

Swine_1930      YPKLSKSYVNNKGKEVLVLWGVHHPPTSTDQQSLYQNADAYVSVGSSKYDRRFTPEIAAR
SC_1918         YPKLSKSYVNNKGKEVLVLWGVHHPPTGTDQQSLYQNADAYVSVGSSKYNRRFTPEIAAR
1943_HA_Weiss   YPNLKNSYVNKKGKEVLVLWGVHHPSSIKEQQTLYQKENAYVSVVSSNYNRRFTPEIAER
USSR_1977       YPNLSKSYVNNKEKEVLVLWGVHHPSNIEDQKTIYRKENAYVSVVSSNYNRRFTPEIAER
Mexican_Flu     YPKLSKSYINDKGKEVLVLWGIHHPSTSADQQSLYQNADTYVFVGSSRYSKKFKPEIAIR
                **:*.:.:**:.* *******:***.. :  .*::::: ::** * **.*..:* *** *

Swine_1930      PKVRGQAGRMNYYWTLLEPGDTITFEATGNLVAPRYAFALNRGSESGIITSDAPVHDCDT
SC_1918         PKVRDQAGRMNYYWTLLEPGDTITFEATGNLIAPWYAFALNRGSGSGIITSDAPVHDCNT
1943_HA_Weiss   PKVRDQAGRMNYYWTLLEPGDTITFEANGNLIAPWYAFALSRGFESGIITSNASMHECDT
USSR_1977       PKVRGQAGRINYYWTLLEPGDTITFEANGNLIAPWHAFALNRGSGSGIITSNASMDECDT
Mexican_Flu     PKVRDQEGRMNYYWTLVEPGDKITFEATGNLVVPRYAFAMERNAGSGIIISDTPVHDCNT
                ****.* **:******:****.*****.***:.*::***:.:. .**** *::..::*:*
```

*FIG. 3A*

```
Swine_1930      KCQTPHGAINSSLPFQNIHPVTIGECPKYVKSTKLRMVTGLRNIPSIQSRGLFGAIAGFI
SC_1918         KCQTPHGAINSSLPFQNIHPVTIGECPKYVRSTKLRMATGLRNIPSIQSRGLFGAIAGFI
1943_HA_Weiss   KCQTPQGAINSSLPFQNIHPVTIGECPKYVRSTKLRMVTGLRNIPSIQSRGLFGAIAGFI
USSR_1977       KCQTPQGAINSSLPFQNIHPVTIGECPKYVRSTKLRMVTGLRNIPSIQSRGLFGAIAGFI
Mexican_Flu     TCQTPKGAINTSLPFQNIHPITIGKCPKYVKSTKLRLATGLRNIPSIQSRGLFGAIAGFI
                 ****.****:*********.***.*****.*****.:*********************

Swine_1930      EGGWTGLIDGWYGYHHQNGQGSGYAADQKSTQNAIDGITNKVNSVIEKMNTQFTVVGKEF
SC_1918         EGGWTGMIDGWYGYHHQNEQGSGYAADQKSTQNAIDGITNKVNSVIEKMNTQFTAVGKEF
1943_HA_Weiss   EGGWTGMIDGWYGYHHQNEQGSGYAADQKSTQNAIDGITNKVNSVIEKMNTQFTAVGKEF
USSR_1977       EGGWTGMIDGWYGYHHQNEQGSGYAADQKSTQNAIDGITNKVNSVIEKMNTQFTAVGKEF
Mexican_Flu     EGGWTGMVDGWYGYHHQNEQGSGYAADLKSTQNAIDEITNKVNSVIEKMNTQFTAVGKEF
                ******:.********** ******* ******** ******************.*****

Swine_1930      NNLERRIKNLNKKVDDGFLDVWTYNAELLVLLENERTLDFHDSNVKNLYEKARSQLRNNA
SC_1918         NNLERRIENLNKKVDDGFLDIWTYNAELLVLLENERTLDFHDSNVRNLYEKVKSQLKNNA
1943_HA_Weiss   NNLEKRMENLNKKVDDGFLDIWTYNAELLILLENERTLDFHDSNVKNLYEKVKSQLRNNA
USSR_1977       NKLEKRMENLNKKVDDGFLDIWTYNAELLVLLENERTLDFHDSNVKNLYEKVKSQLKNNA
Mexican_Flu     NHLEKRIENLNKKVDDGFLDIWTYNAELLVLLENERTLDYHDSNVKNLYEKVRSQLKNNA
                *:**:*::*:*********:********:*******:*****:*****::***:***

Swine_1930      KEIGNGCFEFYHKCDDACMESVRNGTYDYPKYSEESKLNREEIDGVKLESMMVYQ-----
SC_1918         KEIGNGCFEFYHKCDDACMESVRNGTYDYPKYSEESKLNREEIDGVKLESMGVYQ-----
1943_HA_Weiss   KEIGNGCFEFYHKCNNECMESVKNGTYDYPKYSEESKLNREKIDGVKLESMGVYQ-----
USSR_1977       KEIGNGCFEFYHKCNNECMESVKNGTYDYPKYSEESKLNREKIDGVKLESMGVYQ-----
Mexican_Flu     KEIGNGCFEFYHKCDNTCMESVKNGTYDYPKYSEEAKLNREEIDGVKLESTRIYQ-----
                **************:: *****:************:*****:******* .**

Swine_1930      ------------------------------
SC_1918         ------------------------------
1943_HA_Weiss   ------------------------------
USSR_1977       ------------------------------
Mexican_Flu     STVASSLVLVVSLGAISFWMCSNGSLQCRICI
```

*FIG. 3B*

Phylip-format Dendrogram

*FIG. 3C*

```
Swine_1930      YEELREQLSSVSSFEKFEIFPKTSSWPNHETTRGVTAACPYAGASSFYRNLLWLVKKENS
SC_1918         YEELREQLSSVSSFEKFEIFPKTSSWPNHETTKGVTAACSYAGASSFYRNLLWLTKKGSS
1943_HA_Weiss   YEELREQLSSVSSFERFEIFPKESSWPKHNTARGVTAACSHAGKSSFYRNLLWLTEKDGS
USSR_1977       YEELREQLSSVSSFERFEIFPKERSWPKHNVTRGVTASCSHKGKSSFYRNLLWLTEKNGS
Mexican_Flu     YEELREQLSSVSSFERFEIFPKTSSWPNHDSNKGVTAACPHAGAKSFYKNLIWLVKKGNS
                ***************:******  ***:*:  :****:*.: * .***:**:**.:* .*

Site Sb
Swine_1930      YPKLSKSYVNNKGKEVLVLWGVHHPPTSTDQQSLYQNADAYVSVGSSKYDRRFTPEIAAR
SC_1918         YPKLSKSYVNNKGKEVLVLWGVHHPPTGTDQQSLYQNADAYVSVGSSKYNRRFTPEIAAR
1943_HA_Weiss   YPNLKNSYVNKKGKEVLVLWGVHHPSSIKEQQTLYQKENAYVSVVSSNYNRRFTPEIAER
USSR_1977       YPNLSKSYVNNKEKEVLVLWGVHHPSNIEDQKTLYRKENAYVSVVSSNYNRRFTPEIAER
Mexican_Flu     YPKLSKSYINDKGKEVLVLWGIHHPSTSADQQSLYQNADTYVFVGSSRYSKKFKPEIAIR
                **:*.:**:*.* ********:***..  :*:::*:: ::** * **.*.::*.:::: *
```

*FIG. 4*

```
                                                         Site Sa
Swine_1930      YEELREQLSSVSSFEKFEIFPKTSSWPNHETTRGVTAACPYAGASSFYRNLLWLVKKENS
SC_1918         YEELREQLSSVSSFEKFEIFPKTSSWPNHETTKGVTAACSYAGASSFYRNLLWLTKKGSS
1943_HA_Weiss   YEELREQLSSVSSFERFEIFPKESSWPKHNTARGVTAACSHAGKSSFYRNLLWLTEKDGS
USSR_1977       YEELREQLSSVSSFERFEIFPKERSWPKHNVTRGVTASCSHKGKSSFYRNLLWLTEKNGS
Mexican_Flu     YEELREQLSSVSSFERFEIFPKTSSWPNHDSNKGVTAACPHAGAKSFYKNLIWLVKKGNS
                ***************:******  ***:*:  :****:*.: * .***:**:**.:* .*
             Site Sa
Swine_1930      YPKLSKSYVNNKGKEVLVLWGVHHPPTSTDQQSLYQNADAYVSVGSSKYDRRFTPEIAAR
SC_1918         YPKLSKSYVNNKGKEVLVLWGVHHPPTGTDQQSLYQNADAYVSVGSSKYNRRFTPEIAAR
1943_HA_Weiss   YPNLKNSYVNKKGKEVLVLWGVHHPSSIKEQQTLYQKENAYVSVVSSNYNRRFTPEIAER
USSR_1977       YPNLSKSYVNNKEKEVLVLWGVHHPSNIEDQKTLYRKENAYVSVVSSNYNRRFTPEIAER
Mexican_Flu     YPKLSKSYINDKGKEVLVLWGIHHPSTSADQQSLYQNADTYVFVGSSRYSKKFKPEIAIR
                **:*.:**:*.* ********:***..  :*:::*:: ::** * **.*.::*.:::: *
```

*FIG. 5*

```
1F1    EVQLVQSGGGVVQPRRSLRLSCAASGFTFSS--YAMHWVRQAPGKGLEWVAVISYDGR--
1I20   EVQLVESGGGVVQPGGSLRLSCIASAFNLGI--FGMHWVRQAPGKGLEWVAFIRYDGG--
F18    EVQLVQSGGAVVQPGRSLRLSCAASGFTFSI--YAMHWVRQTPGKGLEWVALISYDGN--
F5     RGQLVQSGGGVVQPGRSLRLSCAASGFVFNV--FAIHWVRQAPGKGLEWLATISYDGL--
       . ***:***.****  ****** **.* :.  :.:****:*******:* * ***

1F1    NKYYADSVKGRFTVSRDNSKNTLYLQMNSLRAEDTSVYYCARELLMD-YYDHI----GYS
1I20   KTFYADSVKGRFTISRDNSKNTLYLQMNSLRTEDTALYYCARDATAD-YYGPG----SYP
F18    NKYYADSVKGRFTISRDNYKNTLYLQMKGLRAEDTALYYCARRITEKGYYNDS----GRP
F5     NKYYADSVKGRITISRDNSKNTLYLQMNSLRAEDTAVYYCVRDSEESTYYGDTMW---VY
       :.:********:*:**** ********:.**.***::***.*    .**.

1F1    P-------GPT------WGQGTLVTVS
1I20   N-----WLDP-------WGQGTLVTVS
F18    N-----WFDP-------WGQGTLVTVS
F5     N-----WFDL-------WGQGTLVTVS
                       **********
```

FIG. 6

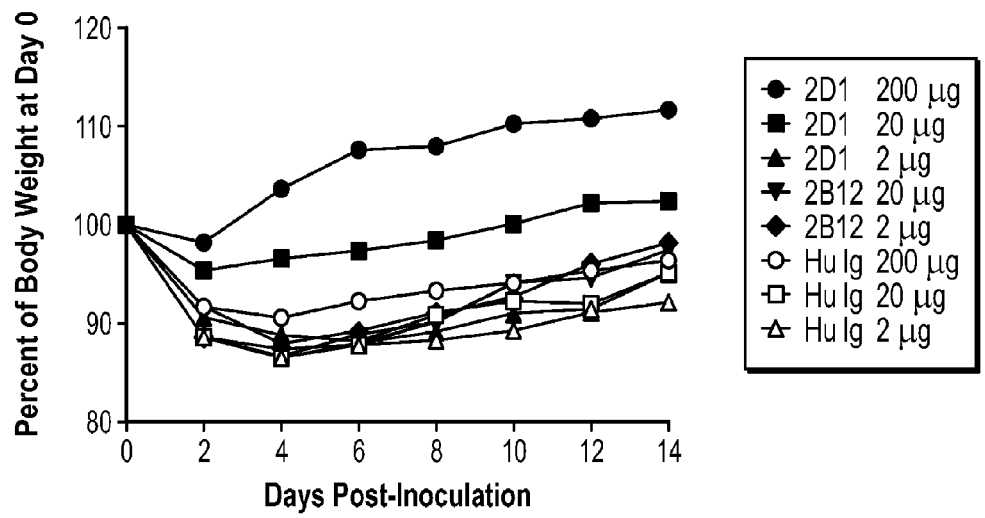

FIG. 7

```
                         53          .          .          .          .          99
A/California/04/2009     KLRGVAPLHLGKCNIAGWILGNPECESLSTASSWSYIVETPSSDNGTCYP
A/South_Carolina/1/1918  KLKGIAPLQLGKCNIAGWLLGNPECDLLLTASSWSYIVETSNSKNGTCYP
A/Puerto_Rico/8/34       RLKGIAPLQLGKCNIAGWLLGNPECDPLSPVRSWSYIVETPNSENGTCYP
A/Brisbane/59/2007       LLKGIAPLQLGNCSVAGWLLGNPECELLISKESWSYIVEKPNPENGTCYP .          .          .          .        145
A/California/04/2009     GDFIDYEELREQLSSVSSFERFEIFPKTSSWPNHDSNKGVTAACPHAGAK
A/South_Carolina/1/1918  GDFIDYEELREQLSSVSSFERFEIFPKTSSWPNHETTKGVTAACSYAGAS
A/Puerto_Rico/8/34       GDFIDYEELREQLSSVSSFERFEIFPKTSSWPNHNTN-GVTAACSHEGKS
A/Brisbane/59/2007       GHFADYEELREQLSSVSSFERFEIFPKESSWPNHTVT-GVSASCSHNGES .          .          .          .        195
A/California/04/2009     SFYKNLIWLVKKGNSYPKLSKSYINDKGKEVLVLWGIHHPSTSADQQSLY
A/South_Carolina/1/1918  SFYRNLLWLTKKGSSYPKLSKSYVNNKGKEVLVLWGVHHPPTGTDQQSLY
A/Puerto_Rico/8/34       SFYRNLLWLTEKEGSYPKLSKNSYVNKKGKEVLVLWGIHHPPNSKEQQNLY
A/Brisbane/59/2007       SFYRNLLWLTGKNGLYPKLSKSYANNKEKEVLVLWGVHHPPNIGDQKALY .          .          .          .        245
A/California/04/2009     QNADTYVFVGSSRYSKKFKPEIAIRPKVRDQEGRMNYYWTLVEPGDKITF
A/South_Carolina/1/1918  QNADAYVSVGSSKYNRRFTPEIAARPKVRDQAGRMNYYWTLLEPGDTITF
A/Puerto_Rico/8/34       QNENAYVSVVTSNYNRRFTPEIAERPKVRDQAGRMNYYWTLLEPGDTITF
A/Brisbane/59/2007       HTFNAYVSVVSSHYSRKFTPEIAKRPKVRDQEGRINYYWTLLEPGDTITF .          .        276
A/California/04/2009     EATGNLVVPRYAFAMERNAGSGITISDTPVHD
A/South_Carolina/1/1918  EATGNLIAPWYAFALNRGSGSGITISDAPVHD
A/Puerto_Rico/8/34       EANGNLIAPRYAFALSRGFGSGITISNASMHE
A/Brisbane/59/2007       EANGNLIAPRYAFALSRGFGSGITNSNAPMDK
```

*FIG. 8C*

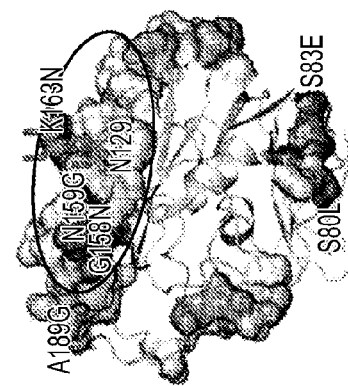
FIG. 9D
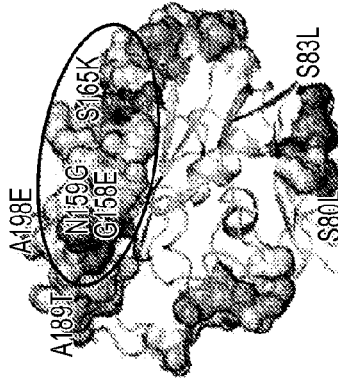
FIG. 9C
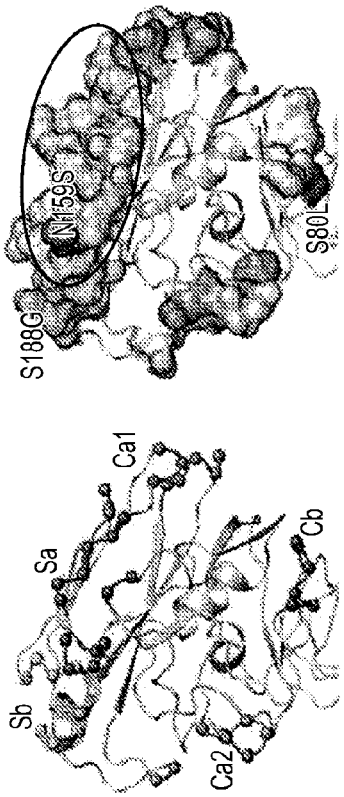
FIG. 9B
FIG. 9A
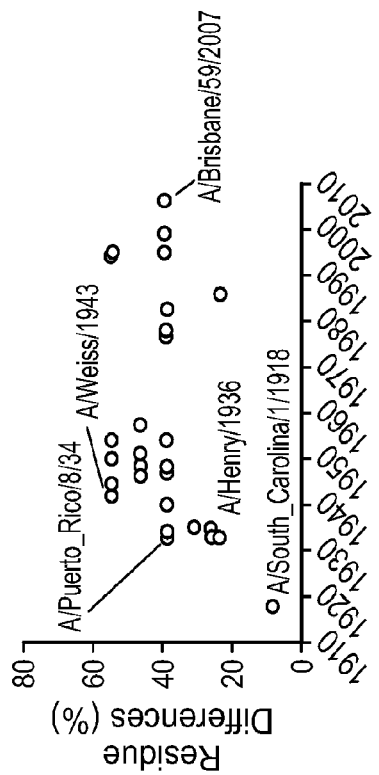
FIG. 9F
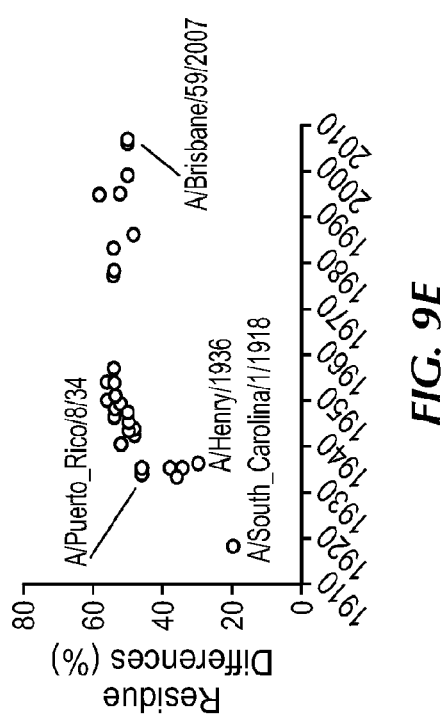
FIG. 9E

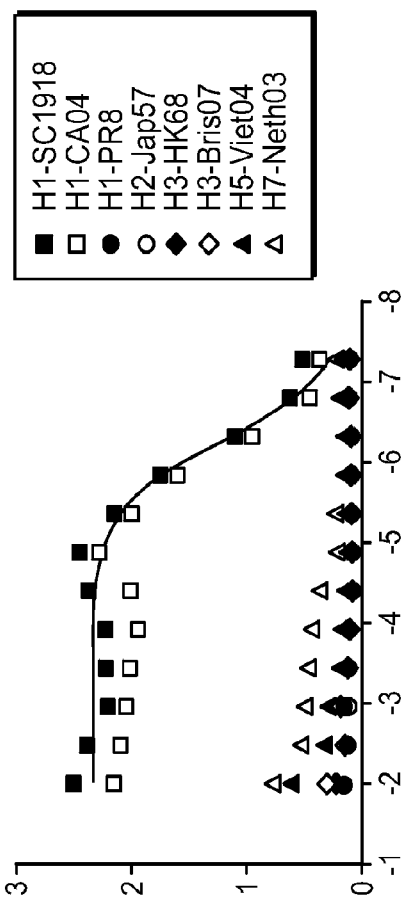
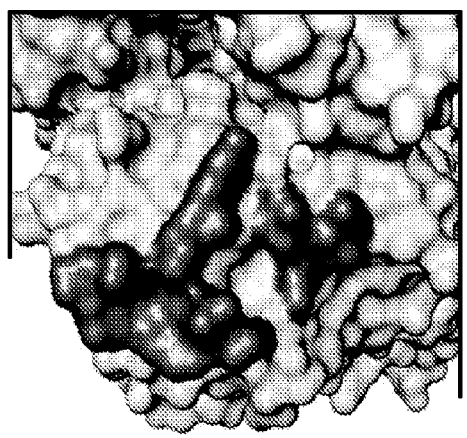
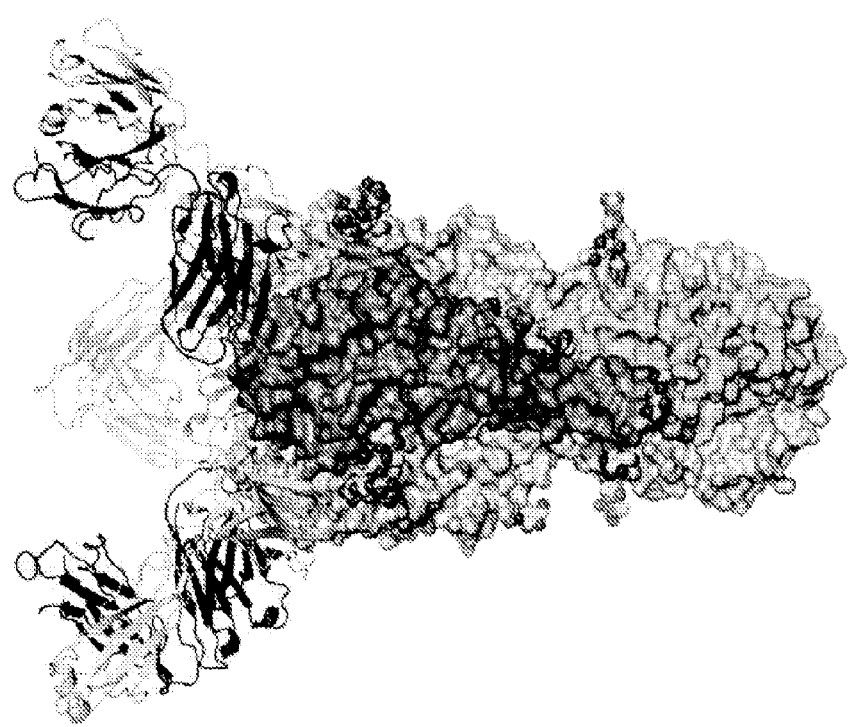
FIG. 10A
FIG. 10B
FIG. 10C

MONOCLONAL ANTIBODIES TO INFLUENZA H1N1 VIRUS USES THEREOF

This application is a national phase application under 35 U.S.C. §371 of International Patent Application No. PCT/US2010/033179 filed Apr. 30, 2010 which claims benefit of priority to U.S. Provisional Application Ser. No. 61/174,415, filed Apr. 30, 2009, the entire contents of both applications being hereby incorporated by reference.

This application claims benefit of priority to U.S. Provisional Application Ser. No. 61/174,415 filed Apr. 30, 2009, the entire content of which are hereby incorporated by reference.

This invention was made with government support under grant numbers U54 AI057157 and U19 AI057229 awarded by the National Institutes of Health. The government has certain rights in the invention.

BACKGROUND OF THE INVENTION

1. Field of the Invention

The present invention relates generally to the fields of virology, immunology and pathology. More particularly, it concerns the development of monoclonal antibodies for use in the diagnosis, prevention and therapy of influenza virus infections, particular those of the H1N1 subtype.

2. Background of the Invention

Influenza, commonly referred to as the flu, is an infectious disease caused by RNA viruses of the family Orthomyxoviridae (the "influenza viruses"), that affects birds and mammals. The name influenza comes from the Italian influenza, meaning "influence" (Latin: influentia). The most common symptoms of the disease are chills, fever, pharyngitis, muscle pains, severe headache, coughing, weakness and general discomfort. Fever and coughs are the most frequent symptoms. In more serious cases, influenza causes pneumonia, which can be fatal, particularly for the young and the elderly. Although it is often confused with the common cold, influenza is a much more severe disease and is caused by a different type of virus. Influenza may produce nausea and vomiting, particularly in children, but these symptoms are more common in the unrelated disease gastroenteritis, which is sometimes called "stomach flu" or "24-hour flu."

Typically, influenza is transmitted from infected mammals through the air by coughs or sneezes, creating aerosols containing the virus, and from infected birds through their droppings. Influenza can also be transmitted by saliva, nasal secretions, feces and blood. Infections also occur through contact with these body fluids or with contaminated surfaces. Flu viruses can remain infectious for about one week at human body temperature, over 30 days at 0° C. (32° F.), and for much longer periods at very low temperatures. Influenza viruses can be inactivated by disinfectants and detergents. As the virus can be inactivated by soap, frequent hand washing reduces the risk of infection.

The symptoms of human influenza were clearly described by Hippocrates roughly 2,400 years ago. Since then, the virus has caused numerous pandemics. Historical data on influenza are difficult to interpret, because the symptoms can be similar to those of other diseases, such as diphtheria, pneumonic plague, typhoid fever, dengue, or typhus. The first convincing record of an influenza pandemic was of an outbreak in 1580, which began in Russia and spread to Europe via Africa. In Rome, over 8,000 people were killed, and several Spanish cities were almost wiped out. Pandemics continued sporadically throughout the 17th and 18th centuries, with the pandemic of 1830-1833 being particularly widespread; it infected approximately a quarter of the people exposed. The most famous and lethal outbreak was the so-called Spanish flu pandemic (type A influenza, H1N1 subtype), which lasted from 1918 to 1919. It is not known exactly how many it killed, but estimates range from 20 to 100 million people. Later flu pandemics were not so devastating. They included the 1957 Asian Flu (type A, H2N2 strain) and the 1968 Hong Kong Flu (type A, H3N2 strain), but even these smaller outbreaks killed millions of people. In later pandemics, antibiotics were available to control secondary infections and this may have helped reduce mortality compared to the Spanish Flu of 1918. An avian strain named H5N1 has recently posed the greatest risk for a new influenza pandemic since it first killed humans in Asia in the 1990's. Each of these pandemics was caused by the appearance of a new strain of the virus in humans. Often, these new strains result from the spread of an existing flu virus to humans from other animal species.

Vaccinations against influenza are usually given to people in developed countries and to farmed poultry. The most common human vaccine is the trivalent influenza vaccine (TIV) that contains purified and inactivated material from three viral strains. Typically, this vaccine includes material from two influenza A virus subtypes and one influenza B virus strain. The TIV carries no risk of transmitting the disease, and it has very low reactivity. A vaccine formulated for one year may be ineffective in the following year, since the influenza virus evolves rapidly, and different strains become dominant. Antiviral drugs can be used to treat influenza, with neuraminidase inhibitors being particularly effective.

In April 2009, a novel H1N1 flu strain that combined genes from human, pig, and bird flu, initially dubbed the "swine flu," emerged in Mexico, the United States, and several other nations. By late April, the H1N1 swine flu was suspected of having killed over 150 in Mexico, and prompted concern that a new pandemic is imminent. The structural similarity to the 1918 Spanish Flu, possibly the greatest medical disaster of all times, highlights to ongoing threat from influenza virus generally, and the H1N1 subtype in particular. Therefore, compositions and methods for the diagnosis, prevention and treatment of this disease remain highly sought after.

SUMMARY OF THE INVENTION

The invention comprises a unique monoclonal antibody that binds the influenza virus HA protein. In one embodiment, the invention comprises a nucleic acid molecule encoding a heavy chain variable region comprising SEQ ID NO:1, 3, 4, 5, 7, 9, or 11. Also provided is nucleic acid molecule encoding a light chain variable region comprising SEQ ID NO: 2, 6, 8, 10 or 12. In particular, the antibody can bind to pandemic H1N1 strains, or strains antigenically related thereto, while not binding to conventional seasonal H1N1 strains.

Further, an antibody, single chain antibody, Fab' antibody fragment or $F(ab')_2$ antibody fragment comprising both heavy and light chain variable regions as specified above are provided. The antibody or antibody fragment may be dispersed in a pharmaceutically acceptable carrier. In particular, the nucleic acid sequences may comprise SEQ ID NO:1 and SEQ ID NO:2, SEQ ID NO:2 and SEQ ID NO: 3, SEQ ID NO:4 and SEQ ID NO:2, SEQ ID NO: 5 and SEQ ID NO:6, SEQ ID NO: 7 and SEQ ID NO: 8, SEQ ID NO: 9 and SEQ ID NO: 10, and SEQ ID NO: 11 and SEQ ID NO:12.

In another embodiment, there is provided a method of neutralizing influenza virus or inhibiting influenza virus replication in a host cell comprising contacting said virus with an antibody or antibody fragment having heavy and light chain variable regions as set forth above. The antibody may be a single chain antibody, and the antibody fragment may be a Fab' or F(ab')$_2$. The contacting may occur in vitro or in vivo. The influenza virus may be located in a human subject, such as an infant or child. The method may further comprise administering to said subject an antiviral. The antibody or antibody fragment may be is administered to said subject more than once. The antibody or antibody fragment may be administered intravenously. The antibody or antibody fragment may prevent or reduce the severity of infection in said subject by influenza virus. In particular, the virus may be the 2009 A (H1N1) pandemic flu.

In yet another embodiment, there is provided a method of diagnosing an influenza virus infection in a subject comprising (a) obtaining a sample from said subject; (b) contacting said sample with an antibody or antibody fragment with heavy and light chain variable regions as specified above; and (c) determining the presence of an influenza virus antigen bound to said antibody. Steps (b) and (c) may comprise an ELISA, RIA or FIA. The subject may be at risk of exposure to influenza virus or may previously have had influenza virus infection. The method may further comprise making a treatment and/or quarantine decision for said subject based on step (c). In particular, the antibody can bind to pandemic H1N1 strains, or strains antigenically related thereto, while not binding to conventional seasonal H1N1 strains, and thus the assay may be diagnostic for pandemic H1N1 such as the 2009 Mexican/California swine flu.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2—Alignments of the Sa and Sb antigenic sites from the HA proteins of select H1N1 viruses. The viruses included are: influenza A/South Carolina/1/18 (H1N1); influenza A/Swine/Iowa/15/30 (H1N1) virus; influenza A/Weiss/43 (H1N1) virus; influenza A/FM/1/47 (H1N1) virus; influenza A/USSR/92/77 (H1N1) virus; influenza A/New Caledonia/20/99 (H1N1) virus; respectively labeled: 1918 (the sequence starting at site 156=SEQ ID NO: 13; 162=SEQ ID NO: 14; 186=SEQ ID NO: 15), Sw/30 (156=SEQ ID NO: 16; 162=SEQ ID NO: 17; 186=SEQ ID NO: 18), 1943 (156=SEQ ID NO: 19; 162=SEQ ID NO: 20; 186=SEQ ID NO: 21), 1947 (156=SEQ ID NO: 22; 162=SEQ ID NO: 23; 186=SEQ ID NO: 24), 1977 (156=SEQ ID NO: 25; 162=SEQ ID NO: 26; 186=SEQ ID NO: 27) or 1999 (156=SEQ ID NO: 28; 162=SEQ ID NO: 29; 186=SEQ ID NO: 30). The alignments are adapted from 13, and the numbering is based upon alignment to the H3 HA of influenza A/Aichi/2/68 (H3N2) virus, as described in Stevens et al. (2004). Black text indicates residues conserved among all six HAs. Blue text highlights differences between 1918 and Sw/30 viruses. Red text indicates residues conserved between 1918 and later viruses. Green residues indicate residues that differ from the 1918 HA. Arrows indicate residues that were changed following selection of mAb neutralization resistant mutants.

Figure 3C:
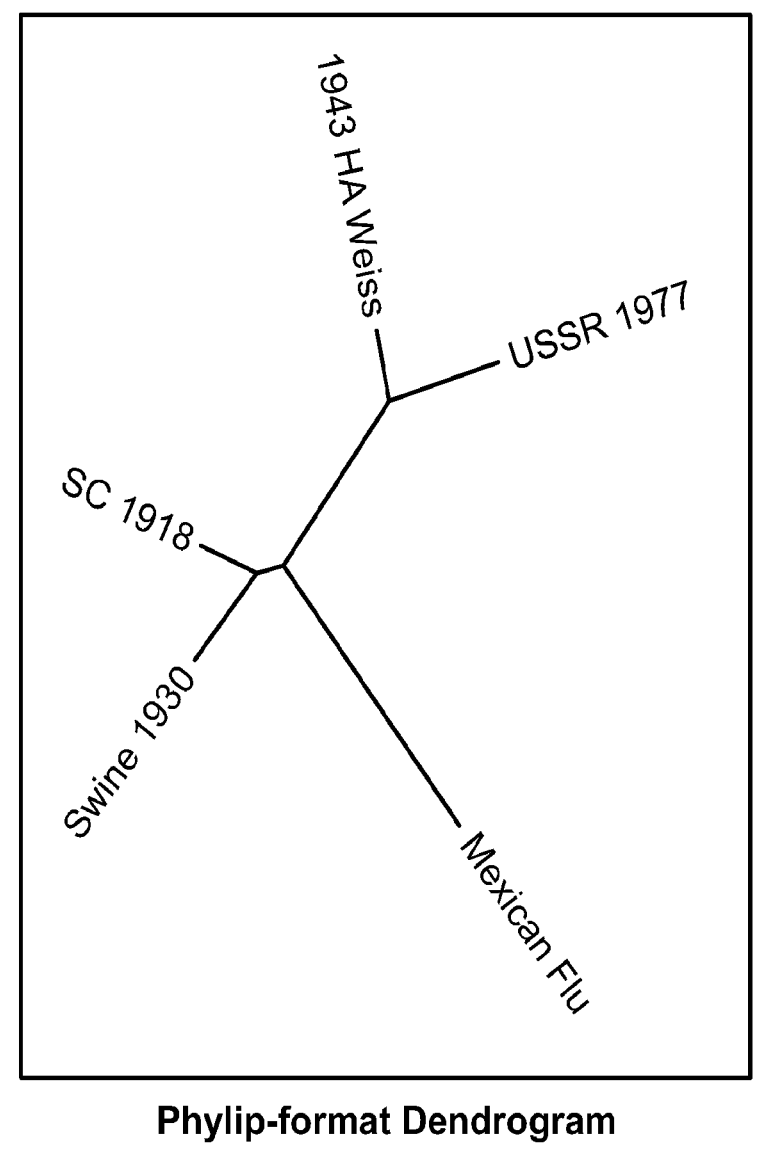

FIG. 3—Alignment of HA sequences of five H1 influenza virus recognized by 1F1 mAbs. (Swine__1930=SEQ ID NO: 31; SC__1918=SEQ ID NO: 32; 1943_HA_Weiss=SEQ ID NO: 33; USSR__1977=SEQ ID NO: 34; Mexican_Flu=SEQ ID NO: 35).

FIG. 4—Alignment of the HA sequences of H1 influenza virus recognized by the 1F1 and 1I20 mAbs compared with 2009 S-0IV. Figure shows conservation of the epitope at the site on 1918; 1F1 recognizes the 1918, 1930, 1943 and 1977. (Swine__1930=SEQ ID NO: 36; SC__1918=SEQ ID NO: 37; 1943_HA_Weiss=SEQ ID NO: 38; USSR__1977=SEQ ID NO: 39; Mexican_Flu=SEQ ID NO: 40).

FIG. 5—Alignment of the HA sequences of H1 influenza virus recognized by the 2B12 2D1 and 4D20 mAbs compared with 2009 S-0IV. Figure shows a high level of conservation of the epitope at the site on 1918. (Swine__1930=SEQ ID NO: 36; SC__1918=SEQ ID NO: 37; 1943_HA_Weiss=SEQ ID NO: 38; USSR__1977=SEQ ID NO: 39; Mexican_Flu=SEQ ID NO: 40).

FIG. 6—Alignment of 1F1 mAb with 1F1-like antibodies. (1F1=SEQ ID NO: 41; 1I20=SEQ ID NO: 42; F18=SEQ ID NO: 43; F5=SEQ ID NO: 44).

FIG. 7—Therapeutic efficacy of 1918 HA-specific monoclonal antibodies against disease cause by the 2009 A (H1N1) virus in mice. In each group, five mice were followed every other day for weight. MAb 2D1 at 200 µg or 20 µg doses prevented weight loss at all time points after virus inoculation, compared to control (p<0.002 for all by ANOVA). Neither mAb 2B12 nor human immunoglobulin (Hu Ig) mediated a statistically significant effect.

FIGS. 8A-C—Crystal structure, phylogeny and antigenic variation in swine flu H1N1 HA. (FIG. 8A) Phylogenetic tree of selected H1 HAs in swine and human. (FIG. 8B) Antigenic structure of CA04 HA from a 2009 H1N1 pandemic virus. A trimer complex is shown in surface representation with antigenic sites highlighted as: Sa site in magenta; Sb site in cyan; Ca site in orange; and Cb site in blue. Sa and Sb sites are located near the receptor-binding site. The Ca site straddles the subunit interface in the trimer. (FIG. 8C) Sequence alignment of membrane-distal domains from representative H1 HAs. Antigenic epitopes are color-coded as in FIG. 8B. (A/California/04/2009=SEQ ID NO: 45; A/South_Carolina/1/1918=SEQ ID NO: 46; A/Puerto_Rico/8/34=SEQ ID NO: 47; A/Brisbane/59/2007=SEQ ID NO:48)

FIGS. 9A-F—Antigenic sites and antigenic variation in H1N1 HAs. (FIG. 9A) Localization of H1 antigenic sites in the membrane-distal domain in close view. Antigenic sites are color-coded as in FIGS. 8A-C. (FIGS. 9B-D) Antigenic variation of seasonal flu H1N1 HAs compared to CA04. Antigenic sites of three H1 HAs are displayed in molecular surface [FIG. 9B, SC1918; FIG. 9C, PR8/34; FIG. 9D, Brisbane 2007 (current seasonal flu vaccine strain)]. Residual differences between CA04 and selected H1 HAs are highlighted based on antigenic regions (Sa, magenta; Sb, cyan; Ca, orange; Cb; blue). The SC1918 HA antigenic surface is well conserved in CA04. In later years (1930-2007), the H1N1 HA antigenic surface became more variable through mutations and importantly, acquired additional N-glycosylation sites (shown as a cartoon with branched sticks) that mask the surface from recognition by neutralizing antibodies. (FIG. 9E) Increased variation over these time periods is shown in the plot of residual differences between CA04 and selected human H1 HAs in the antigenic sites over time. Sequences of H1 HA in the early half of $20^{th}$ century are selected from the NCBI Influenza Virus Resource. After 1977, only the nine H1N1 vaccine strains are shown. (FIG. 9F) Similar plot for the Sa site color-coded by the number of potential N-glycosylation sites in the Sa antigenic region (green, 0 glycans; blue, 1 glycan; orange, 2 glycans; red, 3 glycans).

FIG. 10A-C—Crystal structure of cross-neutralizing antibody 2D1 in complex with SC1918. (FIG. 10A) Antibody 2D1 (the light and heavy chains of the Fab are in red and yellow, respectively) recognizes the Sa site of SC1918 HA, where HA1 is shown in magenta and HA2 in cyan. (FIG. 10B) Footprint of antibody 2D1 on the HA of SC1918 shows the central role of Sa site residues for 2D1 binding. The interacting surface contributed by residues from the Sa site is colored in magenta, whereas residues that contribute to the epitope but are outside of the 'canonical' Sa site are colored in yellow. Sa site residues not in contact with 2D1 are shown in pink. SC1918 and CA04 do not have N-glycosylation sites in the Sa region, whereas Brisbane07, like many other seasonal H1 HAs, have acquired potential glycosylation sites at positions 129 and 163 (italics on surface). (FIG. 10C) Antibody 2D1 exhibits strong binding to both 1918 HA and CA04 HA, but not to PR8 and HAs of other influenza subtypes, as tested in ELISA assay.

DESCRIPTION OF ILLUSTRATIVE EMBODIMENTS

I. The Present Invention

Figure 1:
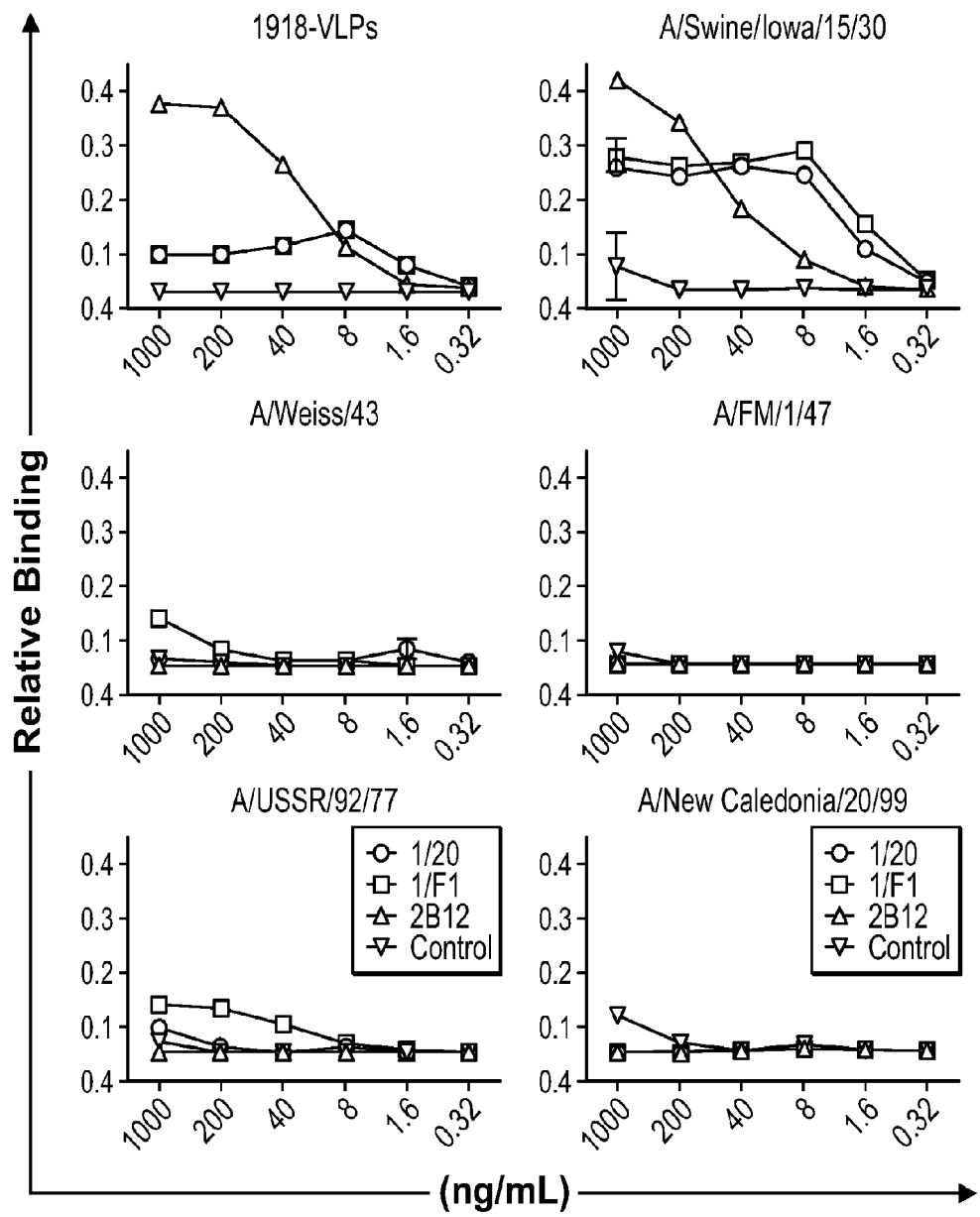
FIG. 1—Binding of human mAbs to representative 20th century H1N1 viruses. Equivalent HA units of 1918 virus-like particles, A/Iowa/Swine/30, A/Weiss/43, A/FM/1/47, A/USSR/92/77 and A/New Caledonia/20/99 influenza viruses were absorbed onto ELISA plates. An ELISA was performed using serial 1:5 dilutions of mAbs 1F1, 1I20, 2B12 or an H5-specific control mAb. Relative binding (y-axis) indicates optical density in ELISA binding assay to absorbed VLPs or virus.

As discussed above, influenza virus is the leading viral cause of severe respiratory tract illness in person of all age, and can also cause severe illness and death in the very young and elderly. Some particularly lethal strains can be fatal to even healthy young adults. All of these patient groups would benefit from more effective antiviral therapeutic options for influenza virus, and in particular, the H1N1 subtype responsible for the 1918 and 2009 influenza outbreaks.

The present invention provides a new monoclonal antibodies that can be delivered in the same manner as currently approved anti-viral therapies. The antibodies bind to the virus fusion protein and causes neutralization of viral infectivity. The antibodies also can be used prophylactically as vaccines, and diagnostically. These and other aspects of the invention are described in detail below.

II. Influenza Virus

A. General

The etiological cause of influenza, the Orthomyxoviridae family of viruses, was first discovered in pigs by Richard Shope in 1931. This discovery was shortly followed by the isolation of the virus from humans by a group headed by Patrick Laidlaw at the Medical Research Council of the United Kingdom in 1933. However, it was not until Wendell Stanley first crystallized tobacco mosaic virus in 1935 that the non-cellular nature of viruses was appreciated.

The first significant step towards preventing influenza was the development in 1944 of a killed-virus vaccine for influenza by Thomas Francis, Jr. This built on work by Australian Frank Macfarlane Burnet, who showed that the virus lost virulence when it was cultured in fertilized hen's eggs. Application of this observation by Francis allowed his group of researchers at the University of Michigan to develop the first influenza vaccine, with support from the U.S. Army. The Army was deeply involved in this research due to its experience of influenza in World War I, when thousands of troops were killed by the virus in a matter of months.

Although there were scares in the State of New Jersey in 1976 (with the Swine Flu), worldwide in 1977 (with the Russian Flu), and in Hong Kong and other Asian countries in 1997 (with H5N1 avian influenza), there have been no major pandemics since the 1968 Hong Kong Flu. Immunity to previous pandemic influenza strains and vaccination may have limited the spread of the virus and may have helped prevent further pandemics.

The influenza virus is an RNA virus of the family Orthomyxoviridae, which comprises five genera: Influenzavirus A, Influenzavirus B, Influenzavirus C, Isavirus and Thogotovirus. The Influenzavirus A genus has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different subtypes based on the antibody response to these viruses. The subtypes that have been confirmed in humans, ordered by the number of known human pandemic deaths, are:

H1N1, which caused Spanish flu in 1918 and has been identified as the subtype of the 2009 outbreak of swine flu originating from Mexico H2N2, which caused Asian Flu in 1957

H3N2, which caused Hong Kong Flu in 1968

H5N1, a pandemic threat in the 2007-08 flu season

H7N7, which has unusual zoonotic potential

H1N2, endemic in humans and pigs

H9N2

H7N2

H7N3

H10N7

Influenzaviruses A, B and C are very similar in structure. The virus particle is 80-120 nanometers in diameter and usually roughly spherical, although filamentous forms can occur. This particle is made of a viral envelope containing two main types of glycoproteins, wrapped around a central core. The central core contains the viral RNA genome and other viral proteins that package and protect this RNA. Unusually for a virus, its genome is not a single piece of nucleic acid; instead, it contains seven or eight pieces of segmented negative-sense RNA. The Influenza A genome encodes 11 proteins: hemagglutinin (HA), neuraminidase (NA), nucleoprotein (NP), M1, M2, NS1, NS2(NEP), PA, PB1, PB1-F2 and PB2.

Hemagglutinin (HA) and neuraminidase (NA) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for antiviral drugs. Furthermore, they are antigens to which antibodies can be raised. Influenza A viruses are classified into subtypes based on antibody responses to HA and NA. These different types of HA and NA form the basis of the H and N distinctions in, for example, H5N1.

Influenza viruses bind through hemagglutinin onto sialic acid sugars on the surfaces of epithelial cells; typically in the nose, throat and lungs of mammals and intestines of birds. The cell imports the virus by endocytosis. In the acidic endosome, part of the hemagglutinin protein fuses the viral envelope with the vacuole's membrane, releasing the viral RNA (vRNA) molecules, accessory proteins and RNA-dependent RNA polymerase into the cytoplasm. These proteins and vRNA form a complex that is transported into the cell nucleus, where the RNA-dependent RNA polymerase begins transcribing complementary positive-sense vRNA. The vRNA is either exported into the cytoplasm and translated, or remains in the nucleus. Newly-synthesised viral proteins are either secreted through the Golgi apparatus onto the cell surface or transported back into the nucleus to bind vRNA and form new viral genome particles. Other viral proteins have multiple actions in the host cell, including degrading cellular mRNA and using the released nucleotides for vRNA synthesis and also inhibiting translation of host-cell mRNAs.

Negative-sense vRNAs that form the genomes of future viruses, RNA-dependent RNA polymerase, and other viral proteins are assembled into a virion. Hemagglutinin and neuraminidase molecules cluster into a bulge in the cell membrane. The vRNA and viral core proteins leave the nucleus and enter this membrane protrusion. The mature virus buds off from the cell in a sphere of host phospholipid membrane, acquiring hemagglutinin and neuraminidase with this membrane coat. As before, the viruses adhere to the cell through hemagglutinin; the mature viruses detach once their neuraminidase has cleaved sialic acid residues from the host cell. After the release of new influenza viruses, the host cell dies.

Because of the absence of RNA proofreading enzymes, the RNA-dependent RNA polymerase makes a single nucleotide insertion error roughly every 10 thousand nucleotides, which is the approximate length of the influenza vRNA. Hence, the majority of newly-manufactured influenza viruses are mutants, causing "antigenic drift." The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

B. The 1918 "Spanish" Flu

The 1918 flu pandemic, commonly referred to as the Spanish Flu, was an influenza pandemic that spread to nearly every part of the world. It was caused by an unusually virulent and deadly Influenza A virus strain of subtype H1N1. Historical and epidemiological data are inadequate to identify the geographic origin of the virus. Most of its victims were healthy young adults, in contrast to most influenza outbreaks which predominantly affect juvenile, elderly, or otherwise weakened patients. The pandemic lasted from March 1918 to June 1920, spreading even to the Arctic and remote Pacific islands. It is estimated that anywhere from 20 to 100 million people were killed worldwide, or the approximate equivalent of one third of the population of Europe, more than double the number killed in World War I. This extraordinary toll resulted from the extremely high illness rate of up to 50% and the extreme severity of the symptoms, suspected to be caused by cytokine storms. The pandemic is estimated to have affected up to one billion people—half the world's population at the time.

Scientists have used tissue samples from frozen victims to reproduce the virus for study. Among the conclusions of this research is that the virus kills via a cytokine storm, an overreaction of the body's immune system, which explains its unusually severe nature and the concentrated age profile of its victims. The strong immune systems of young adults ravaged the body, whereas the weaker immune systems of children and middle-aged adults caused fewer deaths.

The global mortality rate from the 1918/1919 pandemic is not known, but is estimated at 2.5 to 5% of those who were infected died. Note this does not mean that 2.5-5% of the human population died; with 20% or more of the world population suffering from the disease to some extent, a case-fatality ratio this high would mean that about 0.5-1% ($\approx$50 million) of the whole population died. Influenza may have killed as many as 25 million in its first 25 weeks. Older estimates say it killed 40-50 million people while current estimates say 50 million to 100 million people worldwide were killed. This pandemic has been described as "the greatest medical holocaust in history" and may have killed more people than the Black Death.

An effort to recreate the 1918 flu strain (a subtype of avian strain H1N1) was a collaboration among the Armed Forces Institute of Pathology, Southeast Poultry Research Laboratory and Mount Sinai School of Medicine in New York; the effort resulted in the announcement (on Oct. 5, 2005) that the group had successfully determined the virus's genetic sequence, using historic tissue samples recovered by pathologist Johan Hultin from a female flu victim buried in the Alaskan permafrost and samples preserved from American soldiers.

Kobasa et al. (2007) reported that monkeys (*Macaca fascicularis*) infected with the recreated strain exhibited classic symptoms of the 1918 pandemic and died from a cytokine storm—an overreaction of the immune system. This may explain why the 1918 flu had its surprising effect on younger, healthier people, as a person with a stronger immune system would potentially have a stronger overreaction. In December, 2008 research by Yoshihiro Kawaoka of University of Wisconsin linked the presence of three specific genes (termed PA, PB1, and PB2) and a nucleoprotein derived from 1918 flu samples to the ability of the flu virus to invade the lungs and cause pneumonia. The combination triggered similar symptoms in animal testing.

C. The 2009 "Swine" Flu

The 2009 flu pandemic was a global outbreak of a new strain of H1N1 influenza virus, often referred to as "swine flu." The virus was first detected in April 2009 and contains a combination of genes from swine, avian (bird), and human influenza viruses. The outbreak began in the state of Veracruz, Mexico, with evidence that there had been an ongoing epidemic for months before it was officially recognized as such. The Mexican government closed most of Mexico City's public and private facilities in an attempt to contain the spread of the virus. However the virus continued to spread globally, clinics in some areas were overwhelmed by people infected, and the World Health Organization (WHO) and US Centers for Disease Control (CDC) stopped counting cases and in June declared the outbreak to be a pandemic.

While only mild symptoms are experienced by the majority of people, some have more severe symptoms. Mild symptoms may include fever, sore throat, cough, headache, muscle or joint pains, and nausea, vomiting, or diarrhea. Those at risk of a more severe infection include: asthmatics, diabetics, those with obesity, heart disease, the immunocompromised, children with neurodevelopmental conditions, and pregnant women. In addition, even for persons previously very healthy, a small percentage of patients will develop viral pneumonia or acute respiratory distress syndrome. This manifests itself as increased breathing difficulty and typically occurs 3-6 days after initial onset of flu symptoms.

Similar to other influenza viruses, pandemic H1N1 is typically contracted by person to person transmission through respiratory droplets. Symptoms usually last 4-6 days. Those with more severe symptoms or those in an at risk group may benefit from antivirals (oseltamivir or zanamivir). The CDC estimates that, in the United States alone, as of Nov. 14, 2009, there had been 9,820 deaths (range 7,070-13,930) caused by swine flu. Currently, there are almost 15,000 confirmed deaths worldwide.

D. Diagnosis and Treatments

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include:

Body aches, especially joints and throat
Extreme coldness and fever
Fatigue
Headache
Irritated watering eyes
Reddened eyes, skin (especially face), mouth, throat and nose
Abdominal pain (in children with influenza B)

It can be difficult to distinguish between the common cold and influenza in the early stages of these infections, but a flu can be identified by a high fever with a sudden onset and extreme fatigue. Diarrhea is not normally a symptom of influenza in adults, although it has been seen in some human cases of the H5N1 "bird flu" and can be a symptom in children.

Since anti-viral drugs are effective in treating influenza if given early, it can be important to identify cases early. Of the symptoms listed above, the combinations of fever with cough, sore throat and/or nasal conjection can improve diagnostic accuracy. Two decision analysis studies suggest that during local outbreaks of influenza, the prevalence will be over 70%, and thus patients with any of these combinations of symptoms may be treated with neuramidase inhibitors without testing. Even in the absence of a local outbreak, treatment may be justified in the elderly during the influenza season as long as the prevalence is over 15%.

The available laboratory tests for influenza continue to improve. The United States Centers for Disease Control and Prevention (CDC) maintains an up-to-date summary of available laboratory tests. According to the CDC, rapid diagnostic tests have a sensitivity of 70-75% and specificity of 90-95% when compared with viral culture. These tests may be especially useful during the influenza season (prevalence=25%) but in the absence of a local outbreak, or peri-influenza season (prevalence=10%).

Influenza's effects are much more severe and last longer than those of the common cold. Most people will recover in about one to two weeks, but others will develop life-threatening complications (such as pneumonia). Influenza, however, can be deadly, especially for the weak, old or chronically ill. The flu can worsen chronic health problems. People with emphysema, chronic bronchitis or asthma may experience shortness of breath while they have the flu, and influenza may cause worsening of coronary heart disease or congestive heart failure. Smoking is another risk factor associated with more serious disease and increased mortality from influenza.

According to the World Health Organization, "Every winter, tens of millions of people get the flu. Most are only ill and out of work for a week, yet the elderly are at a higher risk of death from the illness. We know the worldwide death toll exceeds a few hundred thousand people a year, but even in developed countries the numbers are uncertain, because medical authorities don't usually verify who actually died of influenza and who died of a flu-like illness." Even healthy people can be affected, and serious problems from influenza can happen at any age. People over 50 years old, very young children and people of any age with chronic medical conditions are more likely to get complications from influenza, such as pneumonia, bronchitis, sinus, and ear infections.

Common symptoms of the flu such as fever, headaches, and fatigue come from the huge amounts of proinflammatory cytokines and chemokines (such as interferon or tumor necrosis factor) produced from influenza-infected cells. In contrast to the rhinovirus that causes the common cold, influenza does cause tissue damage, so symptoms are not entirely due to the inflammatory response. This massive immune response can produce a life-threatening cytokine storm. This effect has been proposed to be the cause of the unusual lethality of both the H5N1 avian influenza, and the 1918 pandemic strain (see above).

In some cases, an autoimmune response to an influenza infection may contribute to the development of Guillain-Barré syndrome. However, as many other infections can increase the risk of this disease, influenza may only be an important cause during epidemics. This syndrome can also be a rare side-effect of influenza vaccines, with an incidence of about one case per million vaccinations.

People with the flu are advised to get plenty of rest, drink plenty of liquids, avoid using alcohol and tobacco and, if necessary, take medications such as paracetamol (acetaminophen) to relieve the fever and muscle aches associated with the flu. Children and teenagers with flu symptoms (particularly fever) should avoid taking aspirin during an influenza infection (especially influenza type B), because doing so can lead to Reye's syndrome, a rare but potentially fatal disease of the liver. Since influenza is caused by a virus, antibiotics have no effect on the infection; unless prescribed for secondary infections such as bacterial pneumonia, they may lead to resistant bacteria. Antiviral medication can be effective, but some strains of influenza can show resistance to the standard antiviral drugs.

The two classes of anti-virals are neuraminidase inhibitors and M2 inhibitors (adamantane derivatives). Neuraminidase inhibitors are currently preferred for flu virus infections. The CDC recommended against using M2 inhibitors during the 2005-06 influenza season.

Antiviral drugs such as oseltamivir (trade name Tamiflu) and zanamivir (trade name Relenza) are neuraminidase inhibitors that are designed to halt the spread of the virus in the body. These drugs are often effective against both influenza A and B, and have been shown to be effective in combatting the recently emerged 2009 "swine" flu. The Cochrane Collaboration reviewed these drugs and concluded that they reduce symptoms and complications. Different strains of influenza viruses have differing degrees of resistance against these antivirals, and it is impossible to predict what degree of resistance a future pandemic strain might have.

The antiviral drugs amantadine and rimantadine are designed to block a viral ion channel (M2 protein) and prevent the virus from infecting cells. These drugs are sometimes effective against influenza A if given early in the infection but are always ineffective against influenza B. Measured resistance to amantadine and rimantadine in American isolates of H3N2 has increased to 91% in 2005. In contrast to neuraminidase inhibitors, amantadine and rimantadine have not proven effect again the 2009 "swine" flu.

III. Producing Monoclonal Antibodies

A. General Methods

It will be understood that monoclonal antibodies binding to influenza virus and related proteins will have utilities in several applications. These include the production of diagnostic kits for use in detecting and diagnosing disease. In these contexts, one may to link such antibodies to diagnostic or therapeutic agents, or use them as capture agents or competitors in competitive assays. Means for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

In the case of human monoclonal antibodies, one may instead simply look for an individual already known to have generated an immune response, in this case, to have been infected with influenza virus. Virtually all adults have significant serum titers of neutralizing antibodies to seasonal influenza viruses, therefore most adults are candidates to donate blood containing B cells from which our method can generate human monoclonal antibodies. In order to identify subjects with immunity to 1918 flu, one could generally obtain blood from subjects who were born prior to 1918, as virtually all humans were infected during that pandemic. The antibody described in this invention was generated in this way, by using peripheral blood from otherwise healthy individuals previously infected with influenza viruses.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33 (ATCC CRL-1668) and HMMA2.5 (Posner et al., 1987). The antibodies in this invention were generated using the HMMA2.5 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). The hybridomas secreting the influenza antibodies in this invention were obtained by electrofusion.

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with oubain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted or single-cell sorted by flow cytometric sorting and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Improved Methods of Antibody Production

Antibodies of the present invention can be prepared with an optimized electrofusion method using a PA-4000/PA-101 apparatus with electrode FE-20/1000 fusion chambers (Cyto Pulse Sciences, Inc.). Fusion volume may be 500 µl. Myeloma cells and EBV-transformed human B cells can be washed with RPMI-1640 and Cytofusion medium (Cyto Pulse Sciences, Inc.). Instrument settings are as follows. Prefusion dielectrophoresis performed for 15 seconds with an alternating current voltage of 70V at 0.8 Mhz. Cells electroporated with a single square-wave high-voltage direct current pulse lasting 0.04 milliseconds. The pulse frequencies and voltages include a single pulse of 300V or multiple pulses of different decreasing voltages from 280V to 260V. Post-fusion dielectrophoresis accomplished for 30 seconds using an alternating current voltage of 20V at 0.08 Mhz. After fusion, cells are allowed to recover in the fusion electrode for 30 minutes at room temperature, harvested, and then washed once with RPMI-1640 prior to plating in multi-well plates for culture.

After fusion, cells are seeded into 96-well microplates at approximately 6,000 B cells per well (for example 18,000 total cells when a 2:1 myeloma to B cell ratio was used in fusion) in complete RPMI-1640 medium containing 20% heat-inactivated FBS, 2.5 µg/ml amphotericin B, 2 mM L-glutamine, 1 mM sodium pyruvate, 50 µg/ml gentamicin, 60 µg/ml tylosin solution, 100 µM hypoxanthine, 0.4 µM aminopterin, 16 µM thymidine (HAT; Sigma) and 0.5 µM ouabain. After seven days of culture, cells are fed by removing 100 µl culture medium followed by addition of an equal volume of fresh medium containing 100 µM hypoxanthine/16 µM thymidine (HT; Sigma). The number of independent colonies in each well is counted 20 days after fusion. Fusion efficiency on a percentage basis is calculated as the mean number of hybridoma colonies per number of input B cells× 100. After initial screening for immunoglobulin (Ig) production by an enzyme-linked immunosorbent assay (ELISA), the hybridoma cells from positive wells are expanded into 24-well plates and cultured in RPMI 1640 containing 20% heat-inactivated FBS, 2 mM glutamine, 1 mM sodium pyruvate and 50 µg/mL gentamicin. Supernatants of the expanded lines are then tested for specificity using an antigen-specific ELISA. The positive hybridoma cells are sub-cloned by serial limiting dilution in 96-well plates at 100, 10, and 0.3 cell-per-well density. The 0.3 cell-per-well limiting dilutions are performed twice to ensure that we generated clones.

To establish optimal drug treatment conditions for selection of human hybridomas, the inventors determined the sensitivity and resistance to drug selection of both transformed B cells and myeloma fusion partner cell lines. Conventional primary B cells die in prolonged culture, but transformed B cells can survive prolonged culture and HAT selection. Human cells are sensitive to ouabain selection, however, therefore the selection of human hybridomas is carried out in the presence of ouabain to eliminate non-fused EBV-transformed B cells. The inventors test the sensitivity of EBV-transformed human B cells to differing concentrations of ouabain and finds the minimum concentration for killing EBV-transformed human B cells to be 0.5 µM. More than 99% of EBV-transformed B cells are killed during seven days of culture in medium containing 0.5 µM ouabain. The inventors then test the resistance of seven myeloma fusion partner cell lines to 0.5 µM ouabain.

Synthetic oligodeoxynucleotides (ODNs) that contain immunostimulatory CpG motifs trigger an immunomodulatory cascade that involves B and T cells, natural killer cells and professional antigen-presenting cells. The inventors propose adding CpG ODNs to the EBV transformation medium for human B cells. In order to enrich for the percentage of antigen-specific B cell numbers in pre-fusion B cell samples, one may transfor smaller numbers of human B cells in multiple wells of 384-well plates using CpG and EBV.

C. Engineering of Antibody Sequences

Hybridomas were cultured, then cells lysed and total RNA extracted. Random hexamers were used with RT to generate cDNA copies of RNA, and then PCR performed using a multiplex mixture of PCR primers expected to amplify all human variable gene sequences. PCR product was cloned into pGemEasy vector, then sequenced by automated DNA sequencing using standard vector primers. Assay of binding and neutralization were performed using antibodies collected from hybridoma supernatants and purified by FPLC, using Protein G columns.

Recombinant full length IgG antibodies were generated by subcloning heavy and light chain Fv DNAs from the cloning vector into a Lonza pConPlusGamma™ plasmid vector, transfected into 293 Freestyle cells or Lonza CHO cells, and antibodies were collected an purified from the CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

IV. Passive Immunization and Treatment of Infection with Anti-Influenza Antibodies A. Formulation and Administration The present invention provides pharmaceutical compositions comprising anti-influenza virus antibodies. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Combination Therapy

In order to increase the effectiveness of the antibody therapy of the present invention, it may be desirable to combine this treatment with other agents effective at treating or preventing influenza virus infections, e.g., oseltamivir (Tamiflu™) and zanamivir (Relenza™). This process may involve administering to the patient the antibody of the present invention the other agent(s) at the same time. This may be achieved by use of a single pharmaceutical composition that includes both agents, or by administering two distinct compositions at the same time, wherein one composition includes the antibody of the present invention and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the antibody treatment of the present invention is "A" and the secondary treatment is "B":

| | | | | | | |
|---|---|---|---|---|---|---|
| A/B/A | B/A/B | B/B/A | A/A/B | A/B/B | B/A/A | A/B/B/B |
| B/A/B/B | B/B/B/A | B/B/A/B | A/A/B/B | A/B/A/B | A/B/B/A | |
| B/B/A/A | B/A/B/A | B/A/A/B | A/A/A/B | B/A/A/A | A/B/A/A | |
| A/A/B/A | | | | | | |

Administration of the secondary agent will follow general protocols for that drug, taking into account the toxicity, if any. It is expected that the treatment cycles would be repeated as necessary.

i. Oseltamivir

Oseltamivir is an antiviral drug that is used in the treatment and prophylaxis of both Influenzavirus A and Influenzavirus B infection. Like zanamivir, oseltamivir is a neuraminidase inhibitor. It acts as a transition-state analogue inhibitor of influenza neuraminidase, preventing progeny virions from emerging from infected cells.

Oseltamivir was the first orally active neuraminidase inhibitor commercially developed. It is a prodrug, which is hydrolysed hepatically to the active metabolite, the free carboxylate of oseltamivir (GS4071). It was developed by U.S.-based Gilead Sciences and is currently marketed by Hoffmann-La Roche (Roche) under the trade name Tamiflu®. In Japan, it is marketed by Chugai Pharmaceutical Co., which is more than 50% owned by Roche. Oseltamivir is generally available by prescription only.

Roche estimates that 50 million people have been treated with oseltamivir. The majority of these have been in Japan, where an estimated 35 million have been treated.

In 2009, with increasing fears about the potential for a new influenza pandemic, oseltamivir has received substantial media attention. Governments, corporations, and even some private individuals are stockpiling the drug (which is discouraged by government bodies). Production is currently sufficient to meet the demand for seasonal influenza and for government stockpiling. It is possible that shortages could recur in the event of an actual influenza pandemic.

Oseltamivir is indicated for the treatment and prevention of infections due to influenza A and B virus in people at least one year of age. The usual adult dosage for treatment of influenza is 75 mg twice daily for 5 days, beginning within 2 days of the appearance of symptoms and with decreased doses for children and patients with renal impairment. Oseltamivir may be given as a preventive measure either during a community outbreak or following close contact with an infected individual. Standard prophylactic dosage is 75 mg once daily for patients aged 13 and older, which has been shown to be safe and effective for up to six weeks. The importance of early treatment is that the NA protein inhibition is more effective within the first 48 hours. If the virus has replicated and infected many cells the effectiveness of this medication will be severely diminished, especially over time.

It has been suggested that co-administration of oseltamivir with probenecid could extend a limited supply of oseltamivir. Probenecid reduces renal excretion of the active metabolite of oseltamivir. One study showed that 500 mg of probenecid given every six hours doubled both the peak plasma concentration ($C_{max}$) and the half-life of oseltamivir, increasing overall systemic exposure (AUC) by 150 percent. Although the evidence for this interaction comes from a study by Roche, it was publicised only in October 2005 by a doctor who had reviewed the data. Probenecid was used in similar fashion during World War II to extend limited supplies of penicillin. It is still used to increase penicillin concentrations in serious infections.

Oseltamivir is prescribed as capsules (containing oseltamivir phosphate 98.5 mg equivalent to oseltamivir 75 mg) and as a powder for oral suspension (oseltamivir phosphate equivalent to oseltamivir 12 mg/mL).

As with other antivirals, resistance to the agent was expected with widespread use of oseltamivir, though the emergence of resistant viruses was expected to be less frequent than with amantadine or rimantadine. The resistance rate reported during clinical trials up to July 2004 was 0.33% in adults, 4.0% in children, and 1.26% overall. Mutations conferring resistance are single amino acid residue substitutions in the neuraminidase enzyme.

Mutant H3N2 influenza A virus isolates resistant to oseltamivir were found in 18% of a group of 50 Japanese children treated with oseltamivir. This rate was similar to another study where resistant isolates of H1N1 influenza virus were found in 16.3% of another cohort of Japanese children. Several explanations were proposed by the authors of the studies for the higher-than-expected resistance rate detected. First, children typically have a longer infection period, giving a longer time for resistance to develop. Second, the more recent study is purported to have used more rigorous detection techniques than previous studies.

High-level resistance has been detected in one girl suffering from H5N1 avian influenza in Vietnam. She was being treated with oseltamivir at time of detection. Others have described resistance development in two more Vietnamese patients suffering from H5N1, and compare their cases with six others. They suggest that the emergence of a resistant strain may be associated with a patient's clinical deterioration. They also note that the recommended dosage of oseltamivir does not always completely suppress viral replication, a situation that could favor the emergence of resistant strains.

The genetic sequence for the neuraminidase enzyme is highly conserved across virus strains. This means that there are relatively few variations, and there is also evidence that variations that do occur tend to be less "fit." Thus, mutations that convey resistance to oseltamivir may also tend to cripple the virus by giving it an otherwise less-functional enzyme. The lack of variation in neuraminidase gives two advantages to oseltamivir and zanamivir, the drugs that target that enzyme. First, these drugs work on a broader spectrum of influenza strains. Second, the development of a robust, resistant virus strain appears to be less likely.

ii. Zanamivir

Zanamivir is a neuraminidase inhibitor used in the treatment of and prophylaxis of both Influenzavirus A and Influenzavirus B. Zanamivir was the first neuraminidase inhibitor commercially developed. It is currently marketed by GlaxoSmithKline under the trade name Relenza®, and was developed by a team of scientists at the Victorian College of Pharmacy at Monash University in Melbourne, Australia.

Both Influenza A and B cause illness, however Influenza A is the more virulent strain. Influenza A is responsible for both the common 'seasonal flu' and notable influenza pandemics such as the Spanish flu of 1918, while the Influenza virus B does not cause pandemics. Between 1990 to 2000, nine significant outbreaks of influenza A caused many deaths in England and Wales, compared to just four outbreaks of influenza B.

The approval of Relenza® in the United States was controversial. In 1999 a Food and Drug Administration (FDA) advisory committee voted 13 to 4 not to approve the drug because of limited data on efficacy and safety concerns. The drug was approved later in 1999.

Relenza® is a part of a range of neuraminidase inhibitor medications. This medication was designed to attack the infected host cells, preventing the virus from spreading throughout other cells in the body and thus reducing the amount of time the virus can survive.

In 1990 licensing of zanamivir was sold to Glaxo, which is now known as GlaxoSmithKline (GSK). In 1999, the product was approved for marketing in the US and subsequently has been registered by GSK in a total of 70 countries. (GlaxoSmithKline News release, 2006) Tamiflu®, Relenza®'s main competitor, was proven in 2006 to not be as effective at treating influenza viruses as Relenza®. As a result in August 2006 Germany announced that it would buy 1.7 million doses of Relenza® as part of its preparation strategy against bird flu.

Zanamivir proved to be a potent and effective inhibitor of influenza neuraminidase. It works by binding to the active site of the neuraminidase protein, rendering the influenza virus unable to escape its host cell and infect others. It is also an inhibitor of influenza virus replication in vitro and in vivo; however this did not necessarily translate into a successful clinical treatment for influenza. In clinical trials it was found that zanamivir was able to reduce the time to symptom resolution by 1.5 days if therapy was started within 48 hours of the onset of symptoms.

Relenza® is a safe and effective treatment for influenza, but must be administered soon after the first symptoms appear. Six to 12 hours is ideal. In most countries the drugs can only be obtained with a doctor's prescription, and usually the time taken to get a prescription renders them ineffective.

A further limitation is the poor oral bioavailability of zanamivir. This meant that oral dosing was impossible, limiting dosing to the parenteral (that is, intravenous) routes. This restricted its usage when treating the elderly because it may induce bronchospasm. Zanamivir, therefore, is administered by inhalation—a route that was chosen for patient compliance with therapy. But this route of administration is not acceptable to many in the community.

Zanamivir is specific to the influenza virus, has not been known to cause toxic effects, and does not spread around through the body's systemic circulation. It also shows no signs of viral resistance. However, due to a lack of reports or evidence about its toxicity, the FDA does not license it for use in children under 7 years of age.

Relenza® is at least as effective as Tamiflu® and has fewer side effects, including nausea and headaches, according to one report. The report, based on data compiled from the companies' clinical trials and from subsequent studies, also says there is no evidence of resistance to Relenza®, compared with resistance levels of up to 18% in those taking Tamiflu®.

V. Antibody Conjugates

Antibodies of the present invention may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemilluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase.

Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

VI. Immunodetection Methods

In still further embodiments, the present invention concerns immunodetection methods for binding, purifying, removing, quantifying and otherwise generally detecting influenza virus and its associated antigens. While such methods can be applied in a traditional sense, another use will be in quality control and monitoring of vaccine and other virus stocks, where antibodies according to the present invention can be used to assess the amount or integrity (i.e., long term stability) of H1 antigens in viruses.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of influenza virus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing influenza virus, and contacting the sample with a first antibody in accordance with the present invention, as the case may be, under conditions effective to allow the formation of immunocomplexes.

These methods include methods for purifying influenza virus or related antigens from a sample. The antibody will preferably be linked to a solid support, such as in the form of a column matrix, and the sample suspected of containing the influenza virus or antigenic component will be applied to the immobilized antibody. The unwanted components will be washed from the column, leaving the influenza virus antigen immunocomplexed to the immobilized antibody, which is then collected by removing the organism or antigen from the column.

The immunobinding methods also include methods for detecting and quantifying the amount of influenza virus or related components in a sample and the detection and quantification of any immune complexes formed during the binding process. Here, one would obtain a sample suspected of containing influenza virus or its antigens, and contact the sample with an antibody that binds influenza virus or components thereof, followed by detecting and quantifying the amount of immune complexes formed under the specific conditions. In terms of antigen detection, the biological sample analyzed may be any sample that is suspected of containing influenza virus or influenza virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to influenza virus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the influenza virus or influenza virus antigen is added to the wells. After binding and washing to remove non-specifically bound immune complexes, the bound antigen may be detected. Detection may be achieved by the addition of another anti-influenza virus antibody that is linked to a detectable label. This type of ELISA is a simple "sandwich ELISA." Detection may also be achieved by the addition of a second anti-influenza virus antibody, followed by the addition of a third antibody that has binding affinity for the second antibody, with the third antibody being linked to a detectable label.

In another exemplary ELISA, the samples suspected of containing the influenza virus or influenza virus antigen are immobilized onto the well surface and then contacted with the anti-influenza virus antibodies of the invention. After binding and washing to remove non-specifically bound immune complexes, the bound anti-influenza virus antibodies are detected. Where the initial anti-influenza virus antibodies are linked to a detectable label, the immune complexes may be detected directly. Again, the immune complexes may be detected using a second antibody that has binding affinity for the first anti-influenza virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present invention contemplates the use of competitive formats. This is particularly useful in the detection of influenza virus antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors proposes the use of labeled influenza virus monoclonal antibodies to determine the amount of influenza virus antibodies in a sample. The basic format would include contacting a known amount of influenza virus monoclonal antibody (linked to a detectable label) with influenza virus antigen or particle. The influenza virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

2. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

3. Immunodetection Kits

In still further embodiments, the present invention concerns immunodetection kits for use with the immunodetection methods described above. As the influenza virus antibodies are generally used to detect influenza virus or influenza virus antigens, the antibodies will be included in the kit. The immunodetection kits will thus comprise, in suitable container means, a first antibody that binds to influenza virus or influenza virus antigen, and optionally an immunodetection reagent.

In certain embodiments, the influenza virus antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of the influenza virus or influenza virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present invention will also typically include a means for containing the antibody, antigen, and any other reagent containers in close confinement for commercial sale. Such containers may include injection or blow-molded plastic containers into which the desired vials are retained.

VII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Subjects.

Volunteers born in 1915 or earlier were recruited. 50 mL of peripheral venous blood was obtained from each subject following written informed consent by a clinical collaborator.

Antigen.

Recombinant A/South Carolina/1/1918 virus HA was generated in a baculovirus expression system and purified, as described (Stevens et al., 2004).

Production of mAbs.

PBMCs were obtained from eight donors by density gradient centrifugation of whole heparinized blood. B cells were transformed in 384-well plates with approximately 1000 B cells per well by in vitro culture in medium with CpG ODN 10103 (Coley) and EBV (supernate from cell line B95.8). Supernates from the resulting cell lines were tested for reactivity with 1918 HA by ELISA. Hybridomas were generated using cells from wells containing reactive lines by fusion to the HMMA2.5 non-secreting myeloma cell line (Posner et al., 1987) using electrofusion followed by HAT/ouabain drug selection, as described (Yu et al., 2008). When hybridomas formed colonies, lines were screened using anti-1918 HA ELISA; positive lines were cloned by limiting dilution. Supernates of high-density cultures were produced in CEL-Line Devices (BD Biosciences). Purified and concentrated preparations of each of the antibodies were prepared by FPLC using protein G conjugated resin on an AKTA instrument (GE Healthcare) followed by concentration and buffer exchange using ultra centrifugal filter devices (Millipore).

Characterization of mAbs.

The isotype and subclass of secreted mAbs were determined by ELISA. Nucleotide sequences of variable gene segments were determined from cloned cDNA generated by RT-PCR amplification of cellular mRNA using variable gene specific primers designed to amplify antibody genes from all gene families (Weitkamp et al., 2003). Identity of the gene segments and mutations from the germline sequences were determined by alignment using the ImMunoGeneTics database (imgt.cines.fr:8104) (Ruiz et al., 2000).

Viruses and Plasmids.

The following viruses were propagated in 10-day-old embryonated chicken eggs: A/Weiss/43; A/FM/1/47; A/USSR/92/77; A/New Caledonia/20/99; A/swine/Iowa/15/30. The sequences of the HA genes of these viruses used were confirmed by RT-PCR and cDNA sequence analysis. Influenza A/South Carolina/1/18 virus was prepared as described (Tumpey et al., 2005). Expression plasmids encoding the 1918 HA and NA proteins were described previously (Tumpey et al., 2002; Glaser et al., 2005).

ELISA.

Equivalent HA units of 1918 virus-like particles (VLPs) or of influenza A viruses were diluted in coating buffer (51-2713KC; BD) and adsorbed overnight onto ELISA plates (Nunc). Plates were washed with PBS/0.05% Tween-20 and blocked using blocking solution (555213; BD) or PBS containing 5% FCS at RT for 1 hour. Diluted mAbs were added to plates and incubated at 4° C. for 16 hours. Plates were washed and incubated with HRP-conjugated goat anti-human IgG (H10507; Caltag) for 1 hour. Washed plates were developed using TMB substrate, and the reaction was stopped using 2N sulfuric acid. Optical density was read at 450 nm using an ELISA plate reader.

Production of VLPs.

VLPs were produced by co-transfection of $10^6$ 293T cells with 1 μg each of expression plasmids for the 1918 HA and NA. Two days post-transfection, supernatants were harvested and assayed for HA activity. The ability to produce these hemagglutinating particles in the absence of other viral proteins is consistent with a recent report (Chen et al., 2007).

HAI Assays.

Assays for sera or mAbs were performed according to standard protocols (WHO, 1982). Briefly, sera were diluted initially 1:10 in receptor-destroying enzyme from *Vibrio cholerae* (Denka Seiken, Tokyo). Serial dilutions of sera or mAbs were pre-incubated with 8 HA units of virus per well. Chicken RBCs were added to a final concentration of 0.5%, and the plate was incubated on ice for 30-60 minutes.

Microneutralization Assay.

10 $TCID_{50}$ units of virus was preincubated with dilutions of sera or mAb and used to infect MDCK cells in 96-well plates with six replicates, as described (Mozdzankowska et al., 1997). Neutralizing concentrations were defined as the reciprocal of the highest dilution of serum where 50% of wells were infected, as calculated by the method of Reed and Muench (Reed and Muench, 1938). Specific neutralizing activity of mAbs was calculated as the lowest concentration of mAb that displayed activity.

Biosensor Studies.

The kinetic interaction of mAbs with recombinant 1918 HA protein was determined by surface plasmon resonance using a Biacore 2000 instrument (Biacore, Piscataway, N.J.). Purified 1918 HA protein was diluted to 30 μg/ml in 10 mM sodium acetate, pH 4.5, and covalently immobilized at 5 μl/min by amine coupling to the dextran matrix of a CM5 sensor chip (Biacore AB) with a target density of 1,200 response units (RU). Unreacted active ester groups were blocked with 1M ethanolamine. All five purified 1918 mAbs and a human H5-specific influenza mAb (negative control) at different concentrations ranging from 5 to 500 nM in HBS/Tween-20 buffer (Biacore AB) were injected over the immobilized 1918 HA protein or reference cell surface. Association rates ($K_{on}$), dissociation rates ($K_{off}$), and equilibrium dissociation constants ($K_D$) were calculated by aligning the binding curves globally to fit a 2:1 Langmuir binding model using BIAevaluation 4.1 software. The goodness of each fit was based on the agreement between experimental data and the calculated fits, where the $X^2$ values were below 1.0.

Selection and Characterization of Antibody Escape Mutants.

Mutants were isolated as described (Caton et al., 1982; Yewdell et al., 1979). Briefly, escape mutant viruses were selected by treatment of Sw/30 virus with excess antibody, followed by recovery of neutralization resistant viruses in eggs. RNA was extracted from virus-infected allantoic fluid, then cDNA was generated by RT-PCR, cloned, sequenced, and aligned to previously determined wt virus HA gene sequences.

Animal Studies.

Female BALB/c (8-week old) mice were inoculated intranasally with 5 $LD_{50}$ in a 50 µl volume of the virulent reconstituted 1918 virus. At 24 hrs after inoculation, we administered 200, 20, 2 or 0.2 µg (approximately 10, 1, 0.1 or 0.01 mg/kg) of 1918-specific mAb or a similarly prepared human mAb to H5 influenza HA (clone IE5), or an equal volume of human IgG, to each mouse, in groups of 11 (highest dose) or 5 (lower doses) mice. Mice were observed for 16 days for weight loss or death. Subsets of 3 animals treated with the highest dose were sacrificed on day 2 and 4 after infection and whole lungs were homogenized in 1 mL of sterile PBS. Virus titer in lung tissue homogenates was determined by plaque titration in MDCK cell monolayer cultures.

Example 2

Results and Discussion

Recent studies suggest the 1918 H1N1 influenza virus was of avian origin (Taubenberger et al., 2005; 2006), and is capable of inducing strong systemic cytokine responses that likely contribute to pathogenesis (Kobasa et al., 2007; Kash et al. 2006). Little is known about naturally occurring adaptive immunity to this virus; however, some elderly survivors are still living. The inventors sought to determine whether survivors exhibited evidence of acquired immunity to the virus. Expression of the 1918 HA antigen allowed him to identify and characterize protective antibodies induced by natural exposure of humans to the 1918 pandemic virus.

The inventors identified a panel of 32 subjects aged 91-101 years (i.e., aged 2 to 12 years in 1918), many of whom recalled a sick family member in the household during the pandemic, which suggested direct exposure to the virus. Of the subjects tested, 100% exhibited serum neutralizing activity against the 1918 virus (mean titer 1:562), and 94% had serologic reactivity to the 1918 HA (as indicated by hemagglutination inhibition assay (HAI) titers of 1:40 or greater; mean titer 1:396), even though these samples were obtained nearly 90 years after the pandemic. In contrast, subjects born after the pandemic exhibited markedly lower rates of positive serum neutralizing tests against 1918 virus (9 of 10 subjects born 1926-35 had titers <1:100, 9 of 10 subjects born 1936-45 had titers ≤1:40, 9 of 10 subjects born 1946-55 had titers ≤1:40).

Peripheral blood mononuclear cells from eight subjects were isolated and B lymphoblastic cell lines generated by transformation; blood from almost all donors tested (7 of 8) yielded transformed cells secreting antibodies binding 1918 HA protein. Supernates from 30 wells of a total of 6578 wells tested contained 1918 HA-specific antibodies, suggesting a minimal frequency of circulating 1918 HA-specific B cells in the donors of approximately 1 in $4.6 \times 10^6$. The inventors collected transformed cells from the wells corresponding to supernates exhibiting the highest levels of specific binding to the 1918 HA (derived from five donors) and fused them to the HMMA2.5 nonsecreting myeloma partner (Posner et al., 1987) using an electrofusion technique (Yu et al., 2008). The inventors isolated 17 unique hybridoma cell lines that secreted antibodies reactive with the 1918 HA from cell lines derived from four of five donors and then segregated the lines by limiting dilution to yield monoclonal antibody (mAb) secreting clones. Screening identified five independent lines with HAI activity against 1918 from three separate donors, which the inventors biologically cloned, and designated mAbs 1I20, 1F1, and 2B12 (donor 6), mAb 4D20 (donor 4) and mAb 2D1 (donor 23).

Sequence analysis of the antibody genes from the clones revealed that the five mAbs were distinct and very highly mutated. Genetic features of the mAbs are shown in Table 1. It was of interest that the 1F1, 2B12 and 2D11 clones shared use of the $V_L$1-44*01 gene segment, suggesting a particular fitness for binding of the 1918 virus HA by the CDR1/2 light chain loops encoded by this $V_L$ gene segment. The three clones, however, were clearly independent as they differed in the location of somatic mutations, $J_L$ segment (1F1) and in heavy chain pairing. The numbers of somatic mutations in the variable regions were exceptionally large, almost twice the median number of 18 mutations found in class-switched memory cells in randomly selected human B cells (Tian et al., 2007). These data likely suggest recurrent optimization of binding affinity through multiple rounds of somatic hypermutation and selection in vivo.

Purified mAbs were assessed by ELISA against a series of representative 20$^{th}$ century H1N1 viruses including human isolates from 1918, 1943, 1947, 1977 and 1999. The inventors also examined reactivity with influenza A/Swine/Iowa/15/30 (H1N1) virus, as the HA sequence of this virus more closely resembles the 1918 HA sequence than does the sequence of any other existing isolate. The mAbs bound to the 1918 HA, with clear cross-reactivity with the 1930 strain, suggesting the remote origin of the antibodies (FIG. 1). The 1F1 clone also bound to a minimal degree to the 1977 strain, a virus that is almost identical to isolates from the early 1950s (Nakajima et al., 1978), and minimally to a 1943 isolate, but not to other post-1930 strains. The mAbs also bound to the corresponding HA expressed on the surface of mammalian cells following transfection of a cDNA encoding the 1918 HA as detected by immunofluorescence microscopy (data not shown). The mAbs did not bind to influenza H3, B, or H5 proteins in ELISA (data not shown). All five antibodies proved to have very high affinities for recombinant 1918 HA protein when tested by surface plasmon resonance, ranging from $5.4 \times 10^{-9}$ to $4.8 \times 10^{-11}$ M (Table 1).

The inventors tested five purified mAbs from three separate donors for inhibitory activity in an HAI assay using 1918 virus-like particles (VLPs) or a panel of H1N1 viruses. The mAbs exhibited specific binding for "old" viruses, including the 1918 virus or viruses that were genetically similar to the 1918 virus (Table 2). Specifically, all five mAbs reacted with 1918 HA by ELISA, by HAI with VLPs of the 1918 strain or with the highly genetically similar influenza A/Swine/30

(H1N1) virus (Sw/30), and by neutralizing assay with reconstituted 1918 virus. Comparable HAI activities were obtained for both 1918 and Sw/30 VLPs in these assays (Table 2). The five clones exhibited specific neutralizing activities ranging from 0.32 to 0.97 µg/mL and HAI activities of 0.18 to 0.47 against the 1918 virus. In contrast, the same mAbs failed to interact with or inhibit human H1N1 viruses isolated in 1943, 1947 or 1999 (data not shown). The 1F1 antibody bound and neutralized the 1977 virus, albeit to a lesser degree than either 1918 or Sw/30 viruses (exhibiting a specific HAI activity of 0.16 µg/mL against the 1977 virus), and to a minimal degree the 1943 virus (data not shown). Again, only 1F1 displayed neutralizing activity against the 1943 or 1977 viruses, with a specific activity of 1.8 and 0.88 µg/mL respectively.

The inventors selected antibody escape mutants for three mAbs using the Sw/30 virus. Nucleotide sequence analysis of the HA genes from these viruses revealed that they had acquired mutations in classical antigenic regions of HA. The 2B12 mutants possessed mutations at residue 166 (K166Q, K166E or K166P) which lies within the Sa antigenic site (FIG. 2), using the previous numbering scheme (Stevens et al., 2004). Escape mutants for 1F1 and 1I20 possessed an identical mutation, P186H, a residue adjacent to the previously defined Sb antigenic site (FIG. 2), which encompasses the α-helix of the receptor binding site in the 1918 HA structure (Stevens et al., 2004; Caton et al., 1982; Brownlee & Fodor, 2001). As expected, incorporation of the Sb antigenic site mutation into VLPs reduced (1I20) or eliminated (1F1) activity of the corresponding mAbs in an HAI assay without affecting binding of 2B 12 (Table 2). The 2D1 and 4D20 mAbs also exhibited reduced HAI activity against the site Sb mutant viruses and VLPs, suggesting they also bound to this site. In contrast, incorporation of the Sa mutation into VLPs abolished activity of 2B12 in the HAI assay, but did not affect the activity of the other four mAbs (Table 2). The 1918 and Sw/30 virus HAs differ by only a single amino acid in each of the Sa and Sb sites (FIG. 2), explaining why these mAbs cross-neutralize both viruses. In contrast, the 1943 isolate contains 7 changes in the Sa site and 7 changes in the Sb site, relative to the 1918 HA sequence, explaining the partial or complete loss of neutralizing ability of the mAbs for these later isolates. Strikingly, 9 of the 12 residues at the Sb site differed between the 1918 and the 1977 virus. The ability of 1F1 to cross-neutralize the 1977 virus is worthy of further investigation, since these data raise the possibility that 1F1 recognizes a novel, more broadly neutralizing epitope. Alternatively, the data may represent epitope recycling such that, despite significant sequence divergence, the 1F1 epitope reappeared. In either case, further characterization of this mAb may suggest strategies to elicit enhanced cross-protective immunity to influenza A viruses of a particular HA subtype.

The inventors tested the five mAbs for therapeutic efficacy in an established mouse model of infection. Mice were inoculated by the intranasal route with the previously reconstructed 1918 virus, and morbidity (measured by weight loss), mortality, and virus replication, were assessed as previously described (Tumpey et al., 2005). Each of the five 1918-specific mAbs tested exhibited therapeutic efficacy when administered one day following infection, preventing death of animals (Table 2). Mice treated with a control (H5 HA-specific) human mAb or human IgG did not survive. Reduced weight loss and lower levels of virus replication in lungs of anti-1918 antibody treated mice on day 4 after infection also revealed a significant protective effect that correlated well with survival data. At lower doses, the mAbs caused a statistically-significant delay to death, relative to the controls.

These studies suggest that B cells responding to viral infections, or their progeny, survive for the life of the host, even nine or more decades after exposure. It is well-established that a subset of plasma cells is long-lived (Manz et al., 1997), and these cells contribute to durable humoral immune responses (Slifka et al., 1998), such as that observed after childhood smallpox vaccination (Amanna et al., 2006; 2007; Crotty et al., 2003; Hammarlund et al., 2003). Memory B cell pools also can be long-lived, sustained in part by antigen-independent polyclonal stimuli (Bernasconi et al., 2002). It is difficult to be absolutely certain that the mAbs isolated here were first stimulated by exposure during the 1918 pandemic. However, the clinical history of the subjects and the high functional specificity of the mAbs for the 1918 strain strongly suggest that recent exposures do not account for this immunity. Likely, boosting by antigenically-related viruses in the early decades of the $20^{th}$ century may have contributed to the ability of these subjects to sustain these B cells. The variable genes of five independent human neutralizing mAbs exhibited a very high frequency of somatic mutations, associated with strong binding constants and high potency. The in vivo efficacy of treatment with these mAb shows that the development of functional adaptive immunity to the pandemic virus did occur in survivors of the 1918 pandemic.

It has long been known that infusion of neutralizing antibodies can protect mice from lethal influenza virus infection, and transfusion of convalescent blood products to 1918 influenza victims may have had a beneficial effect (Luke et al., 2006). Thus, the mAbs described here could serve as potential therapeutics for a re-emergent 1918-like virus. The techniques described herein suggest that it may be possible to recover human antibodies that display a wide array of specificities corresponding to the viruses and other pathogens that have infected an individual during their lifetime.

TABLE 1

Genetic and binding kinetics features of 1918 HA-specific human mAbs

| | mAb | | | | |
|---|---|---|---|---|---|
| | 1F1 | 1I20 | 2B12 | 2D1 | 4D20 |
| | Gene segments | | | | |
| $V_H$ | 3-30*04 | 3-30*02 | 4-30-4*01 | 2-70*01 | 2-26*01 |
| D | 3-22*01 | 3-10*01 | 3-3*01 | 1-26*01 | 4-17*01 |
| $J_H$ | 5*02 | 5*02 | 4*02 | 2*01 | 6*02 |
| $V_L$ | 1-44*01 | 3-15*01 | 1-44*01 | 1-44*01 | 3-21*01 |
| $J_L$ | 2*01 | 1*01 | 3*02 | 3*02 | 1*01 |

TABLE 1-continued

Genetic and binding kinetics features of 1918 HA-specific human mAbs

| | mAb | | | | |
|---|---|---|---|---|---|
| | 1F1 | 1I20 | 2B12 | 2D1 | 4D20 |
| Mutations | | | | | |
| $V_H$ | | 26 | 32 | $19^a$ | 17 |
| N insertions | | 8 | 20 | 15 | 10 |
| P insertions | | 0 | 0 | 0 | 0 |
| D | | 13 | 1 | 2 | 1 |
| $J_H$ | 7 | 2 | 1 | 1 | 1 |
| $V_L$ | 7 | 9 | 18 | 7 | 14 |
| $J_L$ | 3 | 0 | 2 | 0 | 2 |
| $V_L$-$J_L$ junction | 3 | 6 | 6 | 2 | 0 |
| Isotype/subclass | IgG1 | IgG1 | IgG2 | IgG1 | IgG1 |
| Light chain | Lambda | Kappa | Lambda | Lambda | Lambda |
| Binding kinetics to 1918 HA | | | | | |
| $K_a$ (1/Ms) | $3.1 \times 10^4$ | $2.9 \times 10^5$ | $1.8 \times 10^4$ | $3.9 \times 10^4$ | $1.7 \times 10^5$ |
| $K_d$ (1/s) | $1.7 \times 10^{-4}$ | $1.4 \times 10^{-5}$ | $1.2 \times 10^{-4}$ | $1.0 \times 10^{-5}$ | $1.0 \times 10^{-5}$ |
| $K_D$ (M) | $5.4 \times 10^{-9}$ | $4.8 \times 10^{-11}$ | $6.2 \times 10^{-9}$ | $2.5 \times 10^{-10}$ | $1.4 \times 10^{-10}$ |

[a]Includes a naturally-occurring 9 nucleotide insertion starting from the $V_H$ region codon 67.

TABLE 2

Specific HAI activity (μg/mL) of human mAbs against wild-type or escape mutant influenza viruses or VLPs displaying their corresponding HA proteins

| | mAb | | | | |
|---|---|---|---|---|---|
| Antigen | 1F1 | 1I20 | 2B12 | 2D1 | 4D20 |
| Sw/30 viruses | | | | | |
| Wild-type | 0.04 | 0.08 | 1.25 | 0.08 | 0.04 |
| P186H (site Sb) | > | > | 1.25 | ND | ND |
| K166E (site Sa) | 0.04 | 0.04 | > | ND | ND |
| K166Q (site Sa) | 0.04 | 0.04 | > | ND | ND |
| 1918 VLPs | | | | | |
| Wild-type | 0.08 | 0.16 | 0.31 | 0.01 | 0.04 |
| P186H (site Sb) | > | 0.63 | 0.31 | 0.01 | 0.04 |
| K166E (site Sa) | <0.04 | 0.08 | > | > | 0.63 |
| K166Q (site Sa) | <0.04 | 0.04 | > | 2.5 | 0.31 |

Specific HAI activity of mAbs was calculated as the lowest concentration of mAb that displayed hemagglutinating activity.
> Indicates activity was not detected at any concentration tested, up to 2.5 μg/mL.
ND indicates not determined.

TABLE 3

Therapeutic efficacy of 1918 HA-specific mAbs against 1918 virus in mice

| Antibody | Experiment | Dose, per mouse (μg)[a] | Weight loss (%)[b] | Virus in lung[c] | Survival (No. protected/ total no.)[d] |
|---|---|---|---|---|---|
| 2B12 | 1 | 200 | 2.3 | 3.8 ± 1.4 | 5/5 |
| | | 20 | 11 | ND | 5/5 |
| | | 2 | 14 | ND | 0/5 |
| 1F1 | 1 | 200 | 1.0 | 3.9 ± 1.4 | 5/5 |
| | | 20 | 12 | ND | 4/5 |
| | | 2 | 10 | ND | 0/5 |
| 1I20 | 1 | 20 | 4.2 | 5.4 ± 0.2 | 5/5 |
| | | 2 | 14 | ND | 0/5 |
| | | 0.2 | 16 | ND | 0/5 |
| 2D1 | 2 | 200 | 3.0 | 3.3 ± 0.5 | 5/5 |
| | | 20 | 10 | 5.1 ± 0.2 | 5/5 |
| | | 2 | 14 | 5.9 ± 0.5 | 0/5 |

TABLE 3-continued

Therapeutic efficacy of 1918 HA-specific mAbs against 1918 virus in mice

| Antibody | Experiment | Dose, per mouse (μg)[a] | Weight loss (%)[b] | Virus in lung[c] | Survival (No. protected/ total no.)[d] |
|---|---|---|---|---|---|
| 4D20 | 2 | 200 | 7.6 | 3.5 ± 0.6 | 5/5 |
| | | 20 | 15 | 5.4 ± 0.5 | 2/5 |
| | | 2 | 17 | 5.8 ± 0.4 | 0/5 |
| Control H5 HA mAb | 1 | 200 | 13 | 6.4 ± 0.3 | 0/5 |
| | | 20 | 15 | ND | 0/5 |
| | | 2 | 18 | ND | 0/5 |
| Control human IgG | 1 | 200 | 15 | 6.3 ± 0.2 | 0/5 |
| | 2 | | 18 | 6.4 ± 0.3 | 0/5 |
| | 1 | 20 | 11 | ND | 0/5 |
| | 2 | | 16 | ND | 0/5 |
| | 1 | 2 | 14 | ND | 0/5 |
| | 2 | | 16 | ND | 0/5 |

The statistical significance of viral titer and morbidity data was determined by using analysis of variance (ANOVA). The statistical significance of mortality data was determined by using the null model likelihood ratio test and the Mann-Whitney test.
[a]Groups of mice were infected intranasally with 5 LD$_{50}$ of 1918 virus and then treated 24 hours later with graded doses of 1918-specific mAb or control antibodies.
[b]Maximum percent weight loss (mean of 5 mice per group); highest antibody dose of each experimental group, P ≤ 0.05 (ANOVA) versus control antibody groups.
[c]Average lung titers of three mice on day 4 post-inoculation, expressed as (log$_{10}$) EID$_{50}$/ml ± SD. All 20 and 200 μg dose experimental groups, P ≤ 0.024 (ANOVA) versus control antibody groups.
ND, not determined.
[d]High antibody dose of each experimental group and 20 μg of 1F1 or 2D11, P ≤ 0.0031 (Mann-Whitney test) versus control antibody groups.

Example 3

Materials & Methods and Results

Microneutralization Assay.

Influenza virus was passaged in Madin-Darby canine kidney (MDCK) cells. The titer of virus stocks was determined in MDCK cell culture monolayers by standard plaque assay. 100 TCID$_{50}$ units of virus was preincubated with dilutions of sera or mAb and then used to infect MDCK cells in 96-well plates, as described (Yu et al., 2008). Six replicate wells were used for each antibody dilution. Neutralizing antibody concentrations were determined and were defined as the reciprocal of the highest dilution of serum where 50% of wells were infected, as calculated by the method of Reed and Muench (Yu et al., 2008). Specific neutralizing activity of mAbs was calculated as the lowest concentration of mAb that displayed neutralizing activity. The minimum concentration of antibody required to neutralize 100 TCID$_{50}$ units of A/Mexico/4108/09 virus was below 40 ng mL$^{-1}$ (267 pM) for 2D1 and 160 ng mL$^{-1}$ (1.1 nM) for 2B12 (Table 5).

Hemagglutination Inhibition Activity (HAI) Assays.

HAI tests using mAbs were performed according to standard protocols (WHO, 1982). Briefly, serial dilutions of purified mAbs in PBS were performed from initial concentration of 5 μg/ml. Sera were diluted initially 1:10 in receptor-destroying enzyme from *Vibrio cholerae* (Denka Seiken, Tokyo). Serial dilutions of mouse positive control sera or human mAbs were pre-incubated with 4 HA units of virus per well. Turkey RBCs were added to a final concentration of 0.5%, and the plate was incubated at room temperature for 30-60 minutes. MAbs 2BD1 and 2D1 antibodies exhibited HAI activity (Table 5). By contrast, the three other 1918 virus HA-specific neutralizing mAbs, 4D20 (site Sa-specific) and 1F1 and 1I20 (site Sb-specific), showed no activity against 2009 A (H1N1) virus, even when tested at 5 μg/mL (Table 5).

MAb 4D20 Kinetics.

Given that the Sa-specific mAb 4D20 did not bind the HA of the 2009 A (H1N1) virus, the inventors explored the role of additional amino acid variations outside the Sa site in alteration of binding and found that reversing either HA protein residue E77 or S78 of the 2009 novel H1N1 to the respective residue of the 1918 virus HA restored binding of mAb 4D20 by biolayer interferometry using human Fc receptor tips and recombinant secreted HA. MAb 4D20 associated more readily with the E77D mutant ($k_a$ 1.7×10$^3$/Ms) than with the S78L ($k_a$ 9.5×10$^2$/Ms) mutant with similar dissociation, resulting in an overall tighter binding of mAb 4D20 to the E77D mutant than to the S78L mutant ($K_D$ 7.2×10$^{-9}$ M versus 1.8×10$^{-8}$ M, respectively).

Selection and Characterization of Antibody Escape Mutants.

The inventors selected and sequenced the HA gene of new MARMs using the wt A/swine/Iowa/15/1930 virus or a recombinant virus generated by reverse genetics containing the CA04 HA and NA proteins in an A/Puerto Rico/8/34 virus background (kindly provided by Dr. Peter Palese) (Caton et al., 1982; Yewdell et al., 1979). Briefly, escape mutant viruses were selected by treatment of virus with excess antibody, followed by recovery of neutralization resistant viruses in 10-day old embryonated chicken eggs. RNA was extracted from virus-infected allantoic fluid, then cDNA was generated by RT-PCR, directly cloned, sequenced, and aligned to previously determined wt virus HA gene sequences. These studies revealed mAb 2B12 selected virus mutants containing either the K166E mutation or a novel mutation at the 125C position (S to I). The mAb 2D1 selected for K166E or K166N mutations in the 2009 HA protein, identical to changes that mediated escape to this antibody in MARMs selected by treatment of the 1918 human or 1930 swine viruses.

Animal Studies.

The inventors tested the mAbs 2B12 and 2D1 for therapeutic efficacy in a non-lethal mouse model of wt CA04 virus infection (Maines et al., 2009). Female BALB/c (8-week old) mice were inoculated intranasally with 1,000 MID$_{50}$ in a 50 μl volume of the CA04 virus, as described (Tumpe et al., 2005). At 24 hrs after inoculation, mice were administered 200, 20, or 2 μg (approximately 10, 1, or 0.1 mg/kg) of mAb 2D1 or 2B12 or an equal volume of human IgG (Sigma) by the intraperitoneal route to each mouse, in groups of 9 mice. Mice were observed for weight loss every other day for 14 days. Subsets of 4 animals treated with the mAbs were euthanized on day 3 after infection and whole lungs were homogenized in 1 mL of sterile PBS. Virus titer in lung tissue homogenates was determined by plaque titration in MDCK cell monolayer cultures. The limit of virus detection was 10$^{0.95}$. MAb 2D1 showed a marked therapeutic efficacy when administered one day after virus inoculation, resulting in a five log$_{10}$ PFU/ml decrease of lung virus titers of lung homogenate at the highest dose (Table 6) and the prevention of weight loss (FIG. 7). MAb 2B12 did not affect replication in vivo at the doses tested.

Recent studies have described some novel antibodies that recognize influenza viruses across subtypes (Ekiert et al., 2009; Sui et al., 2009; Yoshida et al., 2009). This report is the first to describe naturally occurring human mAbs to conserved HA sequences across two pandemic viruses. Antigenic sites are defined as regions for which the binding of specific antibodies is not affected by residue changes at neighboring sites (Urbanski and Margoliash, 1977), however, overlap between sites can occur (Caton et al., 1982; Gerhard et al., 1981). These data suggest that the mAb 4D20 epitope overlaps both the Sa and the Cb site and that its lack of affinity to novel H1N1 is due to changes within or adjacent to the Cb site. The Cb site was defined previously by amino acid residues 78, 79, 80, and 81-83 of the HA (Winter et al., 1981). The variability in residues 77 and the 4D20 binding data shown here suggest this flanking residue also contributes to the Cb antigenic site. The involvement of the residue 125C in recognition of the 2009 virus by mAb 2B12, as found in a MARM we isolated, also reveals extension of the Sa antigenic site beyond conventional definitions. These data suggest that the 2D1 mAb may be promising for diagnostic or therapeutic purposes. However, prophylactic or therapeutic use of a single mAb directed to a site that is often variable in viruses circulating in humans should be considered with caution.

In Table 7, data are presented showing that two of the five 1918 flu antibodies bind to the 2009 pandemic H1N1 (Mexico) strain (top panel). It also shows (bottom three panels) that the antibodies do not bind representative seasonal H1N1 flu strains. These data demonstrate the specificity of the antibodies and their ability to discriminate (in a diagnostic test for instance) the pandemic H1N1 strain from the conventional seasonal strains.

TABLE 4

Alignment of the amino acids in site Sa of the HA of representative swine or human influenza viruses from the 20$^{th}$ century
Amino acid position in indicated site

| | Site Sa | | | Site Sb | Site Ca1 | | Site Ca2 | | Site Cb |
|---|---|---|---|---|---|---|---|---|---|
| | 128 | 156 | 162 | 186 | 169 | 206 | 238 140 | 224 | 77 |
| | \| | \| | \| | * \| | \| | \| | \| \| | \| | \| | a) 1918 pandemic virus

A/South Carolina/1/1918  PN  KKGSS  PKLS<u>K</u>S  PTGTDQQSLYQNA  VNNKG  SSK  EPG  SYAGAS  RD  DLLLTASS TABLE 4-continued Alignment of the amino acids in site Sa of the HA of representative swine or human influenza viruses from the 20th century
Amino acid position in indicated site

|  | Site Sa | Site Sb | Site Ca1 | Site Ca2 | Site Cb |
|---|---|---|---|---|---|
| b) Representative 20th century North American swine viruses | | | | | |
| A/Iowa/15/1930 | -- --EN- | ------ --S---------- | ----- --- --- | P----- -G | -----V-- |
| A/Ohio/23/1935 | -- ---D- | ------ --S-X-------- | ----- --- --- | P----N -G | -----V-- |
| A/Iowa/1945 | -- ---N- | ------ --S---------- | ----- --- --- | P----- -G | -----V-- |
| A/Wisconsin/1/1957 | -- ---D- | ------ --S---------- | ----- --- --- | P----N -G | E----V-- |
| A/Wisconsin/1/1961 | -- --E-- | ------ --S---------- | ----- --- --- | P----N -G | E----V-- |
| A/Wisconsin/2/1966 | -- ----- | ------ --S---------- | ----- --- --- | P----N -G | E--F-V-- |
| A/Iowa/1973 | -- ---N- | ------ --S---------- | ----- --- --- | P----N -G | E--F-V-- |
| A/NewJersey/8/1976 | -D ---N- | ------ --S---------- | ----- --- --- | P----N -G | E----V-- |
| A/Wisconsin/663/1980 | -- ---N- | ------ --S---------- | ----- --- --- | P----N -G | E--F-V-- |
| A/Iowa/24297/1991 | -- ---N- | ------ --S---------- | I---- --- --- | P----N -G | E--F---- |
| A/Minnesota/37866/1999 | -- ---N- | ------ S-S---------- | I---E --- --- | P----N -- | ES-F---- |
| A/Minnesota/1192/2001 | -- ---N- | ------ S-SA--------- | I---E --R --- | PH---- -- | ES-F-T-- |
| A/Wisconsin/87/2005 | -- ---N- | --I--- S-SA--------- | I---E --R --- | PH--TN -- | ES-F---- |
| A/Iowa/01/2006 | -- ---N- | ------ --S----T----- | I---K --- --- | P----N -N | ES-F---- |
| A/Ohio/01/2007 | -- ---N- | --IN-- S-SA--------- | I---E --R --- | PH--TN -- | ES-S---- |
| c) 2009 A(H1N1) human viruses | | | | | |
| A/California/04/2009 | -- ---N- | ------ S-SA----I---- | I-D-- --R --- | PH---K -- | ES-S---- |
| A/Mexico/4108/2009 | -- ---N- | ------ S-SA--------- | I-D-- --R --- | PH---K -- | ES-S---- |
| d) Seasonal human H1N1 influenza viruses | | | | | |
| A/Weiss/1943 | -K E-DG- | -N-KN- SSIKE--T---KE | --K-- --N --- | -H--K- -- | ES--SER- |
| A/Fort Monmouth/1/1947 | -K ETNG- | ------ SNIE--KT--RKE | ----E --N --- | -H--K- -G | ES--SKR- |
| A/USSR/92/1977 | -K E-NG- | -N---- SNIE--KTI-RKE | ----E --N --- | -HK-K- -G | ES-VSKK- |
| A/Brazil/11/1978 | -K E-NG- | -N---- SNIE--KTI-RKE | ----E --N --- | -HK-K- -G | ES-FSKK- |
| A/Chile/1/1983 | -K E-NG- | -N---- SNIE--KTI-RKE | ----E --H --- | -HK-K- -N | ES-FSKK- |
| A/Singapore/6/1986 | -- E-NG- | -N---- SNIG--RAI-HTE | ----E --H --- | -HK-R- -G | ES-FSKK- |
| A/Bayern/7/1995 | -- E-NGL | -N---- SNIG--RAI-HTE | ----E --H --- | -HK-K- -G | ES-FSKE- |
| A/Beijing/262/1995 | -- E-NGL | -N--N- SNIR--RAI-HTE | ----E --H --- | -HK-K- -G | ES-ISKE- |
| A/New Caledonia/20/1999 | -- G-NGL | -N---- -NIGN-RA--HTE | ----E --H --- | -HK-K- -- | E--ISKE- |
| A/Solomon Islands/3/2006 | -- G-NGL | -N---- -NIG--RA--HTE | A---E --H --- | -HN-E- -- | E--ISRE- |
| A/Brisbane/59/2007 | -- G-NGL | -N---- -NIG--KA--HTE | A---E --H --- | -HN-E- -- | E--ISKE- |

Dashes in the table indicate amino acid identity with the 1918 pandemic virus sequence, shown on top line;
*K indicates the K166 amino acid that is most frequently mutated in monoclonal antibody resistant mutant viruses selected with Site Sa-specific neutralizing antibody 2B12.

TABLE 5

Neutralizing or HAI activity of mAbs against Mexico/4108/2009 or 1918 viruses

| | | Specific activity of indicated mAb* (μg/mL) | | | | | Reciprocal titer of antisera** | |
|---|---|---|---|---|---|---|---|---|
| | | Sa-specific | | Sb-specific | | | Mouse anti-Mexico/ | Mouse anti-South Carolina/ |
| Antigen | Test | 2B12 | 2D1 | 4D20 | 1F1 | 1I20 | 4108/2009 | 1/1918 |
| Mex/4108/2009 | Neut Ab | 0.16 | 0.04 | > | > | > | nt | nt |
| | HAI | 0.8 | 0.1 | > | > | > | 320 | 160 |
| A/SC/1/1918 | HAI | 0.32 | 0.025 | 0.04 | 0.04 | 0.28 | 35 | 320 |

*Specific HAI or neutralization activity of mAbs was calculated as the lowest concentration of mAb that displayed inhibition of hemagglutinating or neutralizing activity. Results are the average of 4 tests.
> Indicates activity was not detected at any concentration tested, up to 5 μg/mL.
nt indicates not tested.
**Positive control mouse sera were included and HAI activity, performed by standard methods, are expressed as the reciprocal of the highest dilution of serum inhibiting agglutination of 0.5% of turkey erythrocytes at 4 HA units of virus. Normal mouse serum had a reciprocal titer of less than 10. Results are the average of 4 tests.

TABLE 6

Therapeutic efficacy of 1918 HA-specific mAbs against replication of 2009 A(H1N1) virus in mice

| Antibody | Dose per mouse (µg)* | Lung titers ($\log_{10}$ PFU/ml)† | p value (ANOVA) |
|---|---|---|---|
| 2D1 | 200 | 2.3 ± 1.0 | p < 0.0001 |
|  | 20 | 4.9 ± 0.4 | p < 0.0001 |
|  | 2 | 6.7 ± 0.3 | p = 0.027 |
| 2B12 | 200 | 7.1 ± 0.2 | NS |
|  | 20 | 7.3 ± 0.3 | NS |
|  | 2 | 7.2 ± 0.2 | NS |
| Control human IgG | 200 | 7.1 ± 0.3 | NS |
|  | 20 | 7.2 ± 0.2 | NS |
|  | 2 | 7.1 ± 0.2 | NS |

*Groups of mice were inoculated intranasally with 1,000 $MID_{50}$ of California/04/2009 virus and then treated 24 hours later with graded doses of 1918 HA-specific mAbs or control human IgG.
†Lung titers were determined three days post-inoculation on tissues from four animals in each group. At each of the dose levels, the mean titer differed between control and mAb 2D1 by ANOVA. Rank sum tests also yielded similar results (p = 0.029, p = 0.029, p = 0.08, respectively for 200 µg, 20 µg, or 2 µg).
NS indicates not significant.

TABLE 7

1918 HA-specific mAbs Binding to 2009 H1N1 and Seasonal H1N1 Flu

| Mex/ 4108 | 5.000 | 2.500 | 1.250 | 0.625 | 0.313 | 0.156 | 0.078 | 0.039 | 0.020 | 0.010 | 0.005 | 0.002 |
|---|---|---|---|---|---|---|---|---|---|---|---|---|
| 2B12 | + | + | + | − | − | − | − | − | − | − | − | − |
| 1F1 | − | − | − | − | − | − | − | − | − | − | − | − |
| 1120 | − | − | − | − | − | − | − | − | − | − | − | − |
| 2D1 | + | + | + | + | + | − | − | − | − | − | − | − |
| 4D20 | − | − | − | − | − | − | − | − | − | − | − | − |
| PBS | − | − | − | − | − | − | − | − | − | − | − | − |
| PBS | − | − | − | − | − | − | − | − | − | − | − | − |
| POS CTRL | + | + | + | + | + | + | + | + | + | + | − | − |

A/HK/1870/2008 (2008751647), Birs/59-like

| | | | | | | | | | | | | |
|---|---|---|---|---|---|---|---|---|---|---|---|---|
| 2B12 | − | − | − | − | − | − | − | − | − | − | − | − |
| 1F1 | − | − | − | − | − | − | − | − | − | − | − | − |
| 1120 | − | − | − | − | − | − | − | − | − | − | − | − |
| 2D1 | − | − | − | − | − | − | − | − | − | − | − | − |
| 4D20 | − | − | − | − | − | − | − | − | − | − | − | − |
| PBS | − | − | − | − | − | − | − | − | − | − | − | − |
| PBS | − | − | − | − | − | − | − | − | − | − | − | − |
| POS CTRL | + | + | + | + | + | + | + | + | + | + | − | − |

A/Wisconsin/13/2009 (2009016153), Birs/59-like

| | | | | | | | | | | | | |
|---|---|---|---|---|---|---|---|---|---|---|---|---|
| 2B12 | − | − | − | − | − | − | − | − | − | − | − | − |
| 1F1 | − | − | − | − | − | − | − | − | − | − | − | − |
| 1120 | − | − | − | − | − | − | − | − | − | − | − | − |
| 2D1 | − | − | − | − | − | − | − | − | − | − | − | − |
| 4D20 | − | − | − | − | − | − | − | − | − | − | − | − |
| PBS | − | − | − | − | − | − | − | − | − | − | − | − |
| PBS | − | − | − | − | − | − | − | − | − | − | − | − |
| POS CTRL | + | + | + | + | + | + | + | + | + | − | − | − |

A/Paraguay/67/2009 (2009018910), Birs/59-like

| | | | | | | | | | | | | |
|---|---|---|---|---|---|---|---|---|---|---|---|---|
| 2B12 | − | − | − | − | − | − | − | − | − | − | − | − |
| 1F1 | − | − | − | − | − | − | − | − | − | − | − | − |
| 1120 | − | − | − | − | − | − | − | − | − | − | − | − |
| 2D1 | − | − | − | − | − | − | − | − | − | − | − | − |
| 4D20 | − | − | − | − | − | − | − | − | − | − | − | − |
| PBS | − | − | − | − | − | − | − | − | − | − | − | − |
| PBS | − | − | − | − | − | − | − | − | − | − | − | − |
| POS CTRL | + | + | + | + | + | + | + | + | − | − | − | − |

Example 4

Results and Discussion

Figure 8A:
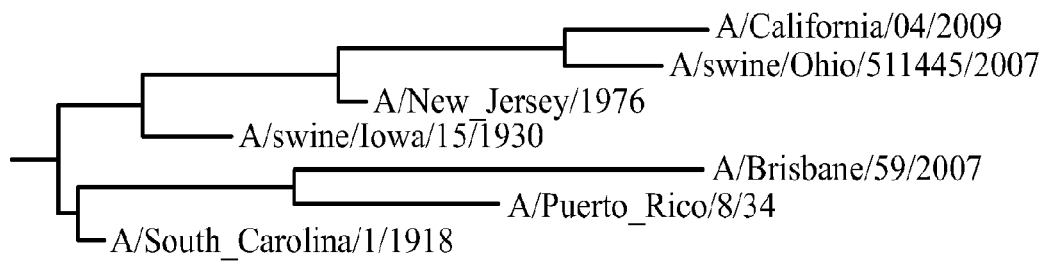

The HA of the 2009 pandemic originated from the swine lineage of H1 HAs and closely resembles current circulating H1-subtype viruses in swine (FIG. 8A) (Smith et al., 2009a; Garten et al., 2009). The human H1 HAs diverged from the swine lineage early in the 20th century, possibly before the 1918 pandemic (Smith et al., 2009b). Descendants of the human 1918 virus continued to circulate until the 1957 pandemic, when they were replaced by H2N2 viruses. H1N1 reappeared in humans in the late 1970's and H1N1 viruses remain a component of seasonal influenza today. In the meantime, H1 viruses continued to circulate in the swine population, remaining antigenically stable (Vincent et al., 2006) and causing only sporadic human infections, including the 1976 outbreak in Fort Dix, N.J. (Zimmer and Burke, 2009; Gaydos et al., 2006).

To understand the structural basis of antigenicity in an emerging pandemic virus, we determined the crystal structure of the HA from a recent swine H1N1 pandemic strain (A/California/04/2009, CA04). The structural analysis reveals that the 2009 H1 HA shares conserved antigenic epitopes with H1 viruses from the early 20th century. This observation is supported by the crystal structure of the 1918 H1 HA in complex with a neutralizing antibody that cross-reacts with both pandemic viruses. These structures shed light on the basis of pre-existing immunity against these new H1N1 pandemic viruses in people born early in the 20th century.

Figure 8B:
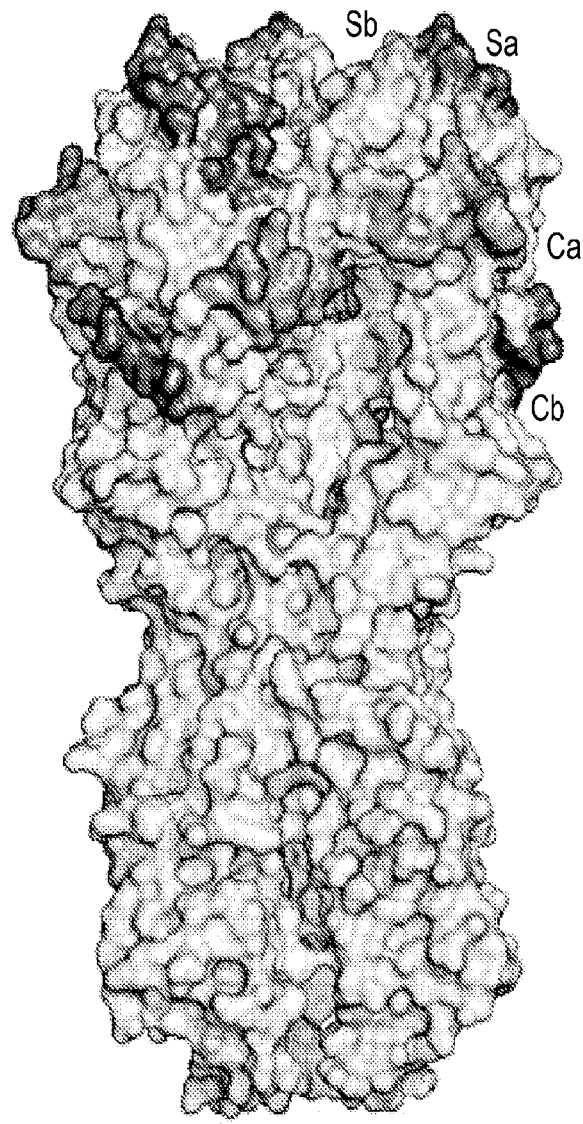

The ectodomain of CA04 HA was expressed in a baculovirus expression system as described (Stevens et al., 2004) and the structure determined by molecular replacement at 2.6 Å resolution (Table S1). The overall structure of CA04 is similar to other H1 HA structures from avian (Lin et al., 2009), swine (Gamblin et al., 2004) and human (Stevens et al., 2004; Gamblin et al., 2004). The HA homotrimer comprises a long extended stem region and a membrane-distal cap that includes the receptor-binding domain and the vestigial esterase domain (FIG. 8B). Whereas the stem region houses the membrane fusion machinery, the membrane-distal domain mediates cell attachment through receptor binding and displays most of the epitopes for antibody recognition.

The antigenic sites of H1 HA are distributed roughly over four conformational epitopes (FIG. 8C) (Canton et al., 1982; Brownlee and Foder, 2001) the Sa and Sb sites proximal to the receptor-binding pocket, the Ca site (Ca1 and Ca2) at the subunit interface, and the Cb site within the vestigial esterase domain (FIGS. 8B and 9A). The majority of the epitopes contain highly variable, protruding loops that can readily be accessed by approaching antibodies. Although the protein sequences are diverse, the CA04 epitopes maintain highly similar conformations to other H1 structures, with the only exception being the Cb site, in which a flexible loop adopts different conformations among different HAs. This structural conservation facilitates comparisons of antigenic structures at the sequence level.

The 2009 pandemic virus displays distinct antigenic properties from seasonal H1 HAs (Garten et al., 2009; Itoh et al., 2009). The previous influenza pandemics of last century were all initiated by the introduction of a new HA subtype into humans. The 2009 pandemic marks the first time that a distant variant of a current circulating HA subtype has been observed to elicit pandemic infections, and would appear to be a consequence of the significant antigenic differences between the seasonal human H1 HAs and the swine O-SIV HAs. Vaccines for current seasonal flu do not provide any cross-reactivity against the 2009 pandemic viruses (Hancock et al., 2009; MMWR, 2009). However, the 2009 pandemic also exhibits an unique pattern of age-related morbidity and mortality, reminiscent of the infamous W-shaped mortality curve observed during the 1918 H1N1 pandemic (Taubengerger and Morens, 2006). The 2009 virus disproportionately affects children and young adults (ages 4-25) in the United States (Centers for Disease Control and Prevention), and surprisingly, the rate of infection decreases with age, with the lowest occurrence in the population of 65 years and older (Lipsitch et al., 2009). A similar trend of age-related infections has also been reported in other countries (Webb et al., 2009). The unexpected, low infection rate in the elderly, the common victims of seasonal flu, suggests pre-existing immunity to the 2009 pandemic viruses (Gamblin et al., 2004).

The CA04 HA structure reveals the molecular basis of its unique antigenic properties. Compared with seasonal H1 HAs, substantial amino-acid differences are found in all four antigenic regions (FIGS. 9B-D). However, the closest relative to CA04 among human viruses is the HA from the 1918 influenza pandemic (A/South Carolina/1/1918, SC1918), with only 20% amino-acid differences in the antigenic epitopes. Moreover, these differences are restricted mainly to the Ca region, with few changes in the Sa, Sb and Cb epitopes. The largely conserved antigenic surface between SC1918 and CA04 suggests a potential for substantial cross-reactivity between the two pandemic strains. Indeed, serological tests suggest that individuals who likely experienced the 1918 Spanish flu carry the highest titers of neutralizing antibodies against the 2009 H1N1 viruses among all age groups (Itoh et al., 2009; Hancock et al., 2009). The antigenic sites of the more recent human H1 HAs are much more divergent when compared to CA04. HAs from the first half of the 20th century (A/Puerto Rico/8/1934, PR8/34) and the current circulating viruses (A/Brisbane/59/2007, Brisbane 2007) differ from CA04 by 46% and 50%, respectively, in the residues corresponding to the antigenic sites. Comparisons with all available HA sequences reveals a steady increase of divergence from 1918 H1 HA during the 1930s up to about 50% residue differences in the antigenic sites that have remained stable since 1940 (FIG. 9E). The early H1N1 viruses would likely present some conserved patches of antigenic surface that would enable the production of CA04 cross-reactive antibodies, but the increased drift in the antigenic sites of later strains would make the generation of such antibodies increasingly rare.

Apart from this drift in the protein sequence in the antigenic sites, glycosylation is used by influenza and other viruses to interfere with surveillance by the host immune system. The acquisition of a glycosylation site masks the protein surface from antibody recognition as the glycans themselves are host-derived and, hence, considered as 'self' by the immune system (Schulze, 1997). The Sa site remained relatively stable among the residues comprising the antigenic surface (FIG. 9F). However, the possibility of a cross-reactive antibody targeting the Sa site has diminished over time by addition of N-glycosylation in the center of the antigenic site. Whereas CA04 and SC1918 have no N-glycosylation sites within or near Sa, the human HAs have gradually acquired up to 3 N-glycosylation sites in the Sa region from 1918 to 2007 (FIG. 9F). Following the same trend as the evolution of protein sequence differences, H1 HAs up to the early 1940's carry zero or one glycosylation site in Sa region, while most of the later isolates harbor 2 or more potential glycosylation sites.

This increased divergence in the antigenic surface of human H1 viruses correlates with decreasing antibody cross-reactivity to CA04 among serum donors when sorted by age (Hancock et al., 2009; MMWR, 2009). SC1918 or 1918-like viruses are the closest relatives of CA04, thus eliciting highest titers of cross-reactive antibodies in the population born before the 1930-40's. By the 1940s, the antigenic structure of the seasonal influenza viruses diverged from 1918 H1N1 and, hence, from CA04 so that only minimal amounts of cross-reactive antibodies could be detected in individuals born after that date. Thus, individuals born after 1940, in general, lack cross-protection from previous exposure to influenza viruses. Current vaccine guidelines put people 65 or older into the group of "less at risk" and thus having lower priority for vaccination (Gamblin et al., 2004). The suggested threshold of 65 is consistent with the trend in the antigenic drift in the H1 HA structures since 1918 that the inventors observe here.

In light of the conservation of the Sa site between the 1918 and CA04 and the neutralizing activity of serum from individuals likely exposed to the 1918 pandemic virus, Sa-specific antibodies are potentially the underlying basis of age-related immunity to the novel H1N1 virus. Recently, a panel of antibodies was isolated from elderly survivors of the 1918 pandemic (Yu et al., 2008). Several of these clones were found to neutralize the 1918 pandemic virus, with little reactivity to the HA of H1N1 isolates after the 1930's. One of these antibodies, 2D1, appeared to map to the Sa site of the 1918 HA on the basis of escape mutations, has similar affinity for the 1918 and CA04 HAs, and was found to neutralize the recent swine H1N1 viruses in vivo (FIG. 10C). To understand the basis of 2D1 cross-reactivity against these two pandemic viruses, we determined the crystal structure of the 2D1 Fab in complex with the 1918 HA. Three copies of the 2D1 Fab are bound to each HA trimer, and recognize an epitope at the apex of the receptor-binding domain (FIG. 10A). The Fab's footprint on the HA largely overlaps with the Sa region, but extends over the boundaries of the site as previously defined (FIG. 10B). Binding of 2D1 to SC1918 HA buries a total surface area of 1502 Å$^2$ (742 Å$^2$ on HA and 760 Å$^2$ on the Fab) with typical, heavy chain-dominant binding (~63% $V_H$, 37% $V_L$). The epitope is conformational and consists primarily of HA residues 125C-129 and 157-169 (FIG. 10B). CDR H1 adopts an unusual, open loop conformation when compared with other Fab structures with identical CDR H1 sequences and a high degree of conservation up to the VD junction (data not shown). This loop makes few contacts with HA and is likely very flexible in solution. Instead, CDRs H2 and H3 dominate the interaction, along with light chain CDRs L1 and L3. The heavy and light chains recognize separate, nearly discontinuous surfaces on HA, with a small cavity being formed at the junction between $V_H$, $V_L$, and HA. Of the 16 HA residues contacting the 2D1 Fab, 9 lie within the previously defined Sa site, accounting for 3/3 salt bridges, 4/7 hydrogen bonds, and 76/105 van der Waals' contacts. Indeed, the Sa site comprises the centerpiece of the antibody-binding surface for 2D1, with the remaining contact residues lining the borders of the Sa site along the periphery of the Fab-HA interface (FIG. 10B).

The antibody-binding site for 2D1 is well conserved in SC1918 and CA04, but not in seasonal HAs (data not shown). A conservative, single amino-acid polymorphism at position 169 in HA1 (Val in SC1918 and Ile in CA04) is the only difference between the Sa sites of these two pandemic viruses and is unlikely to affect 2D1 binding. V169 lies along the periphery of the 2D1 footprint and makes a single van der Waals' contact with CDRH1 (FIG. 10B). In the same region, the 1934 PR8 isolate carries 3 amino-acid variations from SC1918. All three of these mutations lie within the Sa site, including K166N, which would abolish a salt bridge with Asp93 in the 2D1 light chain and G158E, which was found to reduce the affinity of 2D1 for 1918 by 100-fold. Brisbane 2007 shows an even more diverse antigenic surface. Seven amino-acid differences from SC1918 (three of which map to Sa), along with two potential N-glycosylation sites in the center of the antibody-binding region, reveal why 2D1 does not cross-react with the current seasonal viruses. Thus, prior exposure to viruses between 1918 and the early 1930's would likely have elicited antibodies against the Sa site with properties similar to 2D1 and, therefore, these individuals (age ~75+) are expected to have the most potent antibody response against the swine H1N1 viruses. In addition, antibodies that recognize the Sa site of viruses from the 1930's and early 1940's in a manner slightly different from 2D1 could potentially cross-react with S-OIV as well, consistent with the notion that people exposed to influenza during this time period (now age ~65) are also less susceptible to the current pandemic. As mutations and glycosylation sites accumulated in the Sa site beginning in the 1930's, the generation of 2D1-like antibodies in response to seasonal flu or the vaccine strains would have disappeared. Thus, the structural data presented here correlates well with the recent observation that individuals born before 1930 have the greatest neutralizing titers against the swine H1N1 viruses, those born between after 1950 have low titers, and intermediate levels are found in those born between 1930 and 1950.

Taken together, our analysis of the structure of CA04 HA and the 2D1 antibody complex with SC1918 HA has shed considerable light on the observed age-related immunity to the current H1N1 pandemic. Cross-reactive antibodies elicited by infections with H1N1 viruses in the first few decades of the 20$^{th}$ century, along with pre-existing cell-mediated immunity (Xing and Cardona, 2009) contribute to the overall mild symptoms and lower than expected mortality rate in this subset of the population. The high degree of conservation in the Sa site between these viruses and CA04 suggests that 2D1-like antibodies may be very common in those exposed to influenza during this era and potentially the primary determinant of pre-existing immunity to the novel swine H1N1.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,816,567
U.S. Pat. No. 4,867,973
U.S. Pat. No. 4,938,948
U.S. Pat. No. 5,021,236
U.S. Pat. No. 5,196,066
U.S. Pat. No. 5,565,332
"Antibodies: A Laboratory Manual," Cold Spring Harbor Press, Cold Spring Harbor, N.Y., 1988.
Abbondanzo et al., *Am. J. Pediatr. Hematol. Oncol.,* 12(4), 480-489, 1990.
Allred et al., *Arch. Surg.,* 125(1), 107-113, 1990.
Amanna et al., *Immunol Rev* 211, 320-337, 2006.
Amanna et al., *N Engl J Med* 357,1903-1915, 2007.
Atherton et al., *Biol. of Reproduction,* 32, 155-171, 1985.
Bernasconi et al., *Science* 298, 2199-2202, 2002.
Brown et al., *J. Immunol. Meth.,* 12; 130(1), :111-121, 1990.
Brownlee and Fodor, *Phil. Trans. R Soc. Lond. B Biol. Sci.,* 356:1871-1876, 2001.

Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Caton et al., *Cell* 31, 417-427, 1982.
Centers for Disease Control and Prevention. http://www.cdc.gov/h1n1flu/
Chen et al., *J Virol* 81, 7111-7123, 2007.
Crotty et al., *J Immunol* 171, 4969-4973, 2003.
De Jager et al., *Semin. Nucl. Med.* 23(2), 165-179, 1993.
Dholakia et al., *J. Biol. Chem.*, 264, 20638-20642, 1989.
Doolittle and Ben-Zeev, *Methods Mol. Biol.*, 109, :215-237, 1999.
Ekiert et al., *Science*, 324:246-251, 2009.
Gamblin et al., *Science*, 303:1838, 2004.
Garten et al., *Science*, 325:197, 2009.
Gaydos et al., *Emerg. Infect. Dis.*, 12:23, 2006.
Gefter et al., *Somatic Cell Genet.*, 3:231-236, 1977.
Gerhard et al., *Nature*, 290:713-717, 1981.
Glaser et al., *J Virol* 79, 11533-11536, 2005.
Goding, *In: Monoclonal Antibodies: Principles and Practice*, 2d ed., Orlando, Fla., Academic Press, 60-61, 65-66, 71-74, 1986.
Gulbis and Galand, *Hum. Pathol.* 24(12), 1271-1285, 1993.
Hammarlund et al., *Nature Med* 9, 1131-1137, 2003.
Hancock et al., *N. Engl. J. Med.*, 361:1945, 2009.
Itoh et al., *Nature*, 460:1021, 2009.
Kash et al., *Nature* 443, 578-581, 2006.
Khatoon et al., *Ann. of Neurology*, 26, 210-219, 1989.
King et al., *J. Biol. Chem.*, 269, 10210-10218, 1989.
Kobasa et al., *Nature* 445:319-323, 2007.
Kohler and Milstein, *Eur. J. Immunol.*, 6, 511-519, 1976.
Kohler and Milstein, *Nature*, 256, 495-497, 1975.
Lin et al., *Virology*, 392:73, 2009.
Lipsitch et al., *PLoS One* 4, e6895, 2009.
Luke et al., *Ann Intern Med* 145, 599-609, 2006.
Maines et al., *Science*, 325:484-487, 2009.
Manz et al., *Nature* 388, 133-134, 1997.
*MMWR Morb. Mortal. Wkly Rep.*, 58:521, 2009.
Mozdzanowska et al., *A J Virol* 71, 4347-4355, 1997.
Nakajima et al., *Nature* 274, 334-339, 1978.
Nakamura et al., In: *Enzyme Immunoassays: Heterogeneous and Homogeneous Systems*, Chapter 27, 1987.
O'Shannessy et al., *J. Immun. Meth.*, 99, 153-161, 1987.
Owens and Haley, *J. Biol. Chem.*, 259, 14843-14848, 1987.
Posner et al., *Hybridoma* 6, 611-625, 1987.
Potter and Haley, *Meth. Enzymol.*, 91, 613-633, 1983.
Reed et al., *Am J Hygiene* 27, 493-497, 1938.
Ruiz et al., *Nucleic Acids Res* 28, 219-221, 2000.
Schulze, *J. Infect. Dis.*, 176(Suppl 1):S24, 1997.
Slifka et al., *Immunity* 8, 363-372, 1998.
Smith et al., *Nature*, 459:1122, 2009.
Smith et al., *Proc. Natl. Acad. Sci. USA*, 106:11709, 2009.
Stevens et al., *Science* 303, 1866-1870, 2004.
Sui et al., *Nat. Struct. Mol. Biol.*, 16:265-273, 2009.
Taubenberger and Morens, *Emerg. Infect. Dis.*, 12:15, 2006.
Taubenberger et al., *Nature* 437, 889-893, 2005.
Taubenberger, J. K., *Proc Am Philos Soc* 150, 86-112, 2006.
Tian et al., *Mol Immunol* 44, 2173-2183, 2007.
Tumpey et al., *Proc Natl Acad Sci USA* 99, 13849-13854, 2002.
Tumpey et al., *Science* 310, 77-80, 2005.
Urbanski and Margoliash, *J. Immunol.*, 118:1170-1180, 1977.
Vincent et al., *Vet. Microbiol.* 118:212, 2006).
Webb et al., *N. Engl. J. Med.*, 361:1925, 2009.
Weitkamp et al., *J Immunol Methods* 275, 223-237, 2003.
Winter et al., *Nature*, 292:72-75, 1981.
World Health Organization Collaborating Centers for Reference and Research on Influenza, in *Concepts and Procedures for Laboratory-Based Influenza Surveillance*, edited by A. P. Kendal et al., (Centers for Disease Control and Prevention, Atlanta, Ga.), B17-B35, 1982.
Xing and Cardona, *Emerg. Infect. Dis.*, 15:1847, 2009.
Yewdell et al., *Nature* 279, 246-248, 1979.
Yoshida et al., *PLoS Pathog.*, 5:e1000350, 2009.
Yu et al., *J Immunol Methods*, In press; PMID: 18514220, 2008.
Yu et al., *Nature*, 455:532-536, 2008.
Zimmer and Burke, *N. Engl. J. Med.*, 361:279, 2009.

---

The invention claimed is:

1. An expression vector comprising a nucleic acid molecule encoding a heavy chain variable region comprising the sequence of SEQ ID NO: 7.

2. An expression vector comprising a nucleic acid molecule encoding a light chain variable region comprising the sequence of SEQ ID NO: 8.

3. The expression vector of claim 1, wherein said expression vector comprises a promoter operatively linked to said nucleic acid molecule.

4. The expression vector of claim 2, wherein said expression vector comprises a promoter operatively linked to said nucleic acid molecule.

5. An isolated antibody or antigen binding fragment thereof comprising the heavy chain of SEQ ID NO: 7 and the light chain of SEQ ID NO: 8, wherein the antibody or antigen binding fragment thereof is conjugated to a heterologous agent selected from the group consisting of: diagnostic agent, therapeutic agent, and an effector molecule.

6. The isolated antibody or antigen binding fragment thereof of claim 5, dispersed in a pharmaceutically acceptable carrier.

* * * * *

SEQUENCE LISTING

```
<160> NUMBER OF SEQ ID NOS: 48

<210> SEQ ID NO 1
<211> LENGTH: 456
<212> TYPE: PRT
<213> ORGANISM: Homo sapiens

<400> SEQUENCE: 1

Glu Val Gln Leu Val Gln Ser Gly Gly Gly Val Val Gln Pro Arg Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Arg Asn Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ser Val Tyr Tyr Cys
                85                  90                  95
```

Ala Arg Glu Leu Leu Met Asp Tyr Tyr Asp His Ile Gly Tyr Ser Pro
            100                 105                 110

Gly Pro Thr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
    195                 200                 205

Cys Asn Val Asn His Lys Pro Ser Asn Thr Lys Val Asp Lys Arg Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
    435                 440                 445

Ser Leu Ser Leu Ser Pro Gly Lys
    450                 455

<210> SEQ ID NO 2
<211> LENGTH: 217
<212> TYPE: PRT
<213> ORGANISM: Homo sapiens

<400> SEQUENCE: 2

Gln Pro Val Leu Thr Gln Pro Pro Ser Ala Ser Gly Ser Pro Gly Gln
1               5                   10                  15

```
Arg Val Thr Ile Ser Cys Ser Gly Ser Ser Asn Ile Gly Ser Tyr
            20                  25                  30

Thr Val Asn Trp Tyr Gln Gln Leu Pro Gly Thr Ala Pro Lys Leu Leu
        35                  40                  45

Ile Tyr Ser Leu Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Val Tyr Tyr Cys Ala Ala Trp Asp Ser Leu
                85                  90                  95

Ser Ala His Val Val Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
        210                 215

<210> SEQ ID NO 3
<211> LENGTH: 128
<212> TYPE: PRT
<213> ORGANISM: Homo sapiens

<400> SEQUENCE: 3

Arg Gly Gln Leu Val Gln Ser Gly Gly Val Val Gln Pro Gly Arg
1               5                   10                  15

Ser Leu Arg Leu Ser Cys Ala Ala Ser Gly Phe Val Phe Asn Val Phe
            20                  25                  30

Gly Ile His Trp Val Arg Gln Ala Pro Gly Lys Gly Leu Glu Trp Leu
        35                  40                  45

Ala Thr Ile Ser Tyr Asp Gly Leu Asn Lys Tyr Tyr Ala Asp Ser Val
50                  55                  60

Lys Gly Arg Ile Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Ser Glu Glu Ser Tyr Tyr Gly Asp Tyr Met Trp Val
            100                 105                 110

Tyr Asn Trp Phe Asp Leu Trp Gly Gln Gly Thr Leu Val Thr Val Ser
        115                 120                 125

<210> SEQ ID NO 4
<211> LENGTH: 127
<212> TYPE: PRT
<213> ORGANISM: Homo sapiens

<400> SEQUENCE: 4
```

```
Glu Val Gln Leu Val Gln Ser Gly Ala Val Val Gln Pro Gly Arg
1               5                   10                  15

Ser Leu Arg Leu Ser Cys Ala Ala Ser Gly Phe Thr Phe Ser Ile Tyr
            20                  25                  30

Ala Met His Trp Val Arg Gln Thr Pro Gly Lys Gly Leu Glu Trp Val
        35                  40                  45

Ala Leu Ile Ser Tyr Asp Gly Asn Asn Lys Tyr Tyr Ala Asp Ser Val
    50                  55                  60

Lys Gly Arg Phe Thr Ile Ser Arg Asp Asn Tyr Lys Asn Thr Leu Tyr
65                  70                  75                  80

Leu Gln Met Lys Gly Leu Arg Ala Glu Asp Thr Ala Leu Tyr Tyr Cys
            85                  90                  95

Ala Arg Arg Ile Thr Glu Lys Gly Tyr Tyr Asn Asp Ser Gly Arg Pro
            100                 105                 110

Asn Trp Phe Asp Pro Trp Gly Gln Gly Thr Leu Val Thr Val Ser
            115                 120                 125

<210> SEQ ID NO 5
<211> LENGTH: 126
<212> TYPE: PRT
<213> ORGANISM: Homo sapiens

<400> SEQUENCE: 5

Glu Val Gln Leu Val Glu Ser Gly Gly Gly Val Val Gln Pro Gly Gly
1               5                   10                  15

Ser Leu Arg Leu Ser Cys Ile Ala Ser Ala Phe Asn Leu Gly Ile Phe
            20                  25                  30

Gly Met His Trp Val Arg Gln Ala Pro Gly Lys Gly Leu Glu Trp Val
        35                  40                  45

Ala Phe Ile Arg Tyr Asp Gly Gly Lys Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Leu Tyr Tyr Cys
            85                  90                  95

Ala Arg Asp Ala Thr Ala Asp Tyr Tyr Gly Pro Gly Ser Tyr Pro Asn
            100                 105                 110

Trp Leu Asp Pro Trp Gly Gln Gly Thr Leu Val Thr Val Ser
            115                 120                 125

<210> SEQ ID NO 6
<211> LENGTH: 109
<212> TYPE: PRT
<213> ORGANISM: Homo sapiens

<400> SEQUENCE: 6

Asp Ile Arg Leu Thr Gln Ser Pro Ala Thr Leu Ser Val Ser Pro Gly
1               5                   10                  15

Glu Arg Ala Thr Leu Ser Cys Arg Ala Ser His Ser Val Ser Arg Asn
            20                  25                  30

Leu Ala Trp Tyr Gln Gln Lys Pro Gly Arg Ala Pro Arg Leu Leu Val
        35                  40                  45

Tyr Asp Thr Ser Ser Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80
```

```
Glu Asp Phe Ala Val Tyr Tyr Cys Gln Gln Tyr Asn Asn Trp Pro Arg
                85                  90                  95

Thr Phe Gly Gln Gly Thr Lys Val Asp Ile Lys Arg Thr
            100                 105
```

<210> SEQ ID NO 7
<211> LENGTH: 126
<212> TYPE: PRT
<213> ORGANISM: Homo sapiens

<400> SEQUENCE: 7

```
Glu Val Gln Leu Val Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Ser Val Ser Trp Ile Arg Gln Pro Pro Gly Lys Ala Leu Glu
        35                  40                  45

Trp Leu Ala Leu Ile Asp Trp Asp Asp Asp Thr Tyr Tyr Ile Thr Tyr
    50                  55                  60

Ser Ser Ser Leu Lys Thr Arg Leu Thr Ile Ser Lys Asp Thr Ser Lys
65                  70                  75                  80

Ser Gln Val Val Leu Thr Met Thr Asn Met Asp Pro Val Asp Thr Ala
                85                  90                  95

Thr Tyr Tyr Cys Ala Arg Thr Leu Arg Val Ser Gly Asp Tyr Val Arg
            100                 105                 110

Asp Phe Asp Leu Trp Gly Arg Gly Thr Leu Val Thr Val Ser
        115                 120                 125
```

<210> SEQ ID NO 8
<211> LENGTH: 217
<212> TYPE: PRT
<213> ORGANISM: Homo sapiens

<400> SEQUENCE: 8

```
Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Ser Trp Tyr Gln Gln Val Pro Gly Thr Ala Pro Lys Leu Leu
        35                  40                  45

Ile Tyr Gly Asn Asn Glu Arg Pro Ser Gly Val Pro Asp Arg Phe Ser
    50                  55                  60

Gly Ser Lys Ser Ala Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Phe Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175
```

```
Tyr Ala Ala Ser Ser Tyr Leu Ser Leu Thr Pro Glu Gln Trp Lys Ser
            180                 185                 190

His Lys Ser Tyr Ser Cys Gln Val Thr His Glu Gly Ser Thr Val Glu
            195                 200                 205

Lys Thr Val Ala Pro Thr Glu Cys Ser
            210                 215

<210> SEQ ID NO 9
<211> LENGTH: 119
<212> TYPE: PRT
<213> ORGANISM: Homo sapiens

<400> SEQUENCE: 9

Glu Val Gln Leu Val Glu Ser Gly Pro Val Leu Val Lys Pro Thr Glu
1               5                   10                  15

Thr Leu Thr Val Thr Cys Thr Val Ser Gly Phe Ser Val Asp Asn Asp
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Arg Ser Arg Leu Thr Ile Ser Lys Asp Thr Ser Lys Arg Gln Val
65                  70                  75                  80

Val Leu Ser Met Thr Asp Met Asp Pro Val Asp Thr Ala Thr Tyr Tyr
                85                  90                  95

Cys Ala Arg Ala Pro Ser Glu Tyr Ala Ala Met Asp Val Trp Gly Gln
            100                 105                 110

Gly Thr Met Val Thr Val Ser
        115

<210> SEQ ID NO 10
<211> LENGTH: 214
<212> TYPE: PRT
<213> ORGANISM: Homo sapiens

<400> SEQUENCE: 10

Ser Tyr Val Leu Thr Gln Pro Pro Ser Val Ser Val Ala Pro Gly Glu
1               5                   10                  15

Thr Ala Thr Val Thr Cys Gly Gly Asn Asn Ile Gly Ser Lys Ser Val
            20                  25                  30

His Trp Tyr Gln Gln Lys Pro Gly Gln Ala Pro Val Val Val Ile Tyr
        35                  40                  45

Tyr Asp Gly Asp Arg Pro Ser Gly Ile Pro Glu Arg Phe Ser Gly Ser
    50                  55                  60

Asn Ser Gly Asp Thr Ala Thr Leu Thr Ile Ser Arg Val Glu Ala Gly
65                  70                  75                  80

Asp Glu Ala Asp Tyr Tyr Cys Leu Val Trp Asp Tyr Thr Ser Val His
                85                  90                  95

Tyr Val Phe Gly Thr Gly Thr Lys Val Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160
```

```
Val Glu Thr Thr Lys Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
        210

<210> SEQ ID NO 11
<211> LENGTH: 448
<212> TYPE: PRT
<213> ORGANISM: Homo sapiens

<400> SEQUENCE: 11

Glu Val Gln Leu Gln Glu Ser Gly Pro Gly Leu Val Lys Pro Ser Gln
1               5                   10                  15

Thr Leu Ser Leu Thr Cys Asn Val Ser Gly Ser Ile Thr Gly Asp
            20                  25                  30

Tyr Lys Trp Ser Trp Ile Arg Gln Pro Pro Gly Lys Gly Leu Glu Trp
            35                  40                  45

Ile Gly His Ile His Ser Thr Gly Thr Thr Tyr Tyr Asn Pro Ser Leu
    50                  55                  60

Arg Ser Arg Ile Thr Ile Ser Met Asp Thr Ser Lys Asn Asn Leu Ser
65                  70                  75                  80

Leu Arg Leu Thr Ser Val Thr Ala Ala Asp Thr Ala Val Tyr Tyr Cys
            85                  90                  95

Ala Ser His Thr Leu Thr Ser Gly His Tyr Pro Arg Asp Phe Asp Phe
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
            195                 200                 205

Asp His Lys Pro Ser Asn Thr Lys Val Asp Lys Thr Val Glu Arg Lys
            210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Asp Val Ser His Glu Asp
            260                 265                 270

Pro Glu Val Gln Phe Asn Trp Tyr Val Asp Gly Met Glu Val His Asn
            275                 280                 285

Ala Lys Thr Lys Pro Arg Glu Glu Gln Phe Asn Ser Thr Phe Arg Val
            290                 295                 300

Val Ser Val Leu Thr Val Val His Gln Asp Trp Leu Asn Gly Lys Glu
```

```
                305                 310                 315                 320
Tyr Lys Cys Lys Val Ser Asn Lys Gly Leu Pro Ala Pro Ile Glu Lys
                    325                 330                 335

Thr Ile Ser Lys Thr Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Gly Lys
        435                 440                 445

<210> SEQ ID NO 12
<211> LENGTH: 217
<212> TYPE: PRT
<213> ORGANISM: Homo sapiens

<400> SEQUENCE: 12

Ser Tyr Val Leu Thr Gln Pro Pro Ser Val Ser Gly Thr Pro Gly Gln
1               5                   10                  15

Arg Val Ile Ile Ser Cys Ser Gly Tyr Ser Ser Asn Ile Gly Ser Asn
            20                  25                  30

Thr Val Asn Trp Tyr Gln Gln Phe Pro Gly Thr Ala Pro Arg Leu Leu
        35                  40                  45

Ile Tyr Ala Asn Asn Gln Arg Pro Pro Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Asp Asp Glu Ser Asp Tyr Tyr Cys Ala Ala Trp Asp Ser Leu
                85                  90                  95

Asn Gly His Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 13
<211> LENGTH: 5
```

```
<212> TYPE: PRT
<213> ORGANISM: Influenza A virus

<400> SEQUENCE: 13

Lys Lys Gly Ser Ser
1               5

<210> SEQ ID NO 14
<211> LENGTH: 6
<212> TYPE: PRT
<213> ORGANISM: Influenza A virus

<400> SEQUENCE: 14

Pro Lys Leu Ser Lys Ser
1               5

<210> SEQ ID NO 15
<211> LENGTH: 13
<212> TYPE: PRT
<213> ORGANISM: Influenza A virus

<400> SEQUENCE: 15

Pro Thr Gly Thr Asp Gln Gln Ser Leu Tyr Gln Asn Ala
1               5                   10

<210> SEQ ID NO 16
<211> LENGTH: 5
<212> TYPE: PRT
<213> ORGANISM: Influenza A virus

<400> SEQUENCE: 16

Lys Lys Glu Asn Ser
1               5

<210> SEQ ID NO 17
<211> LENGTH: 6
<212> TYPE: PRT
<213> ORGANISM: Influenza A virus

<400> SEQUENCE: 17

Pro Lys Leu Ser Lys Ser
1               5

<210> SEQ ID NO 18
<211> LENGTH: 13
<212> TYPE: PRT
<213> ORGANISM: Influenza A virus

<400> SEQUENCE: 18

Pro Thr Ser Thr Asp Gln Gln Ser Leu Tyr Gln Asn Ala
1               5                   10

<210> SEQ ID NO 19
<211> LENGTH: 5
<212> TYPE: PRT
<213> ORGANISM: Influenza A virus

<400> SEQUENCE: 19

Glu Lys Asp Gly Ser
1               5

<210> SEQ ID NO 20
<211> LENGTH: 6
<212> TYPE: PRT
<213> ORGANISM: Influenza A virus
```

<400> SEQUENCE: 20

Pro Asn Leu Lys Asn Ser
1               5

<210> SEQ ID NO 21
<211> LENGTH: 13
<212> TYPE: PRT
<213> ORGANISM: Influenza A virus

<400> SEQUENCE: 21

Ser Ser Ile Lys Glu Gln Gln Thr Leu Tyr Gln Lys Ala
1               5                   10

<210> SEQ ID NO 22
<211> LENGTH: 5
<212> TYPE: PRT
<213> ORGANISM: Influenza A virus

<400> SEQUENCE: 22

Glu Thr Asp Gly Ser
1               5

<210> SEQ ID NO 23
<211> LENGTH: 6
<212> TYPE: PRT
<213> ORGANISM: Influenza A virus

<400> SEQUENCE: 23

Pro Lys Leu Ser Lys Ser
1               5

<210> SEQ ID NO 24
<211> LENGTH: 13
<212> TYPE: PRT
<213> ORGANISM: Influenza A virus

<400> SEQUENCE: 24

Ser Asn Ile Glu Asp Gln Lys Thr Leu Tyr Arg Lys Glu
1               5                   10

<210> SEQ ID NO 25
<211> LENGTH: 5
<212> TYPE: PRT
<213> ORGANISM: Influenza A virus

<400> SEQUENCE: 25

Glu Lys Asn Gly Ser
1               5

<210> SEQ ID NO 26
<211> LENGTH: 6
<212> TYPE: PRT
<213> ORGANISM: Influenza A virus

<400> SEQUENCE: 26

Pro Asn Leu Ser Lys Ser
1               5

<210> SEQ ID NO 27
<211> LENGTH: 13
<212> TYPE: PRT
<213> ORGANISM: Influenza A virus

<400> SEQUENCE: 27

Ser Asn Ile Glu Asp Gln Lys Thr Ile Tyr Arg Lys Glu
1               5                   10

<210> SEQ ID NO 28
<211> LENGTH: 5
<212> TYPE: PRT
<213> ORGANISM: Influenza A virus

<400> SEQUENCE: 28

Gly Lys Asn Gly Leu
1               5

<210> SEQ ID NO 29
<211> LENGTH: 6
<212> TYPE: PRT
<213> ORGANISM: Influenza A virus

<400> SEQUENCE: 29

Pro Asn Leu Ser Lys Ser
1               5

<210> SEQ ID NO 30
<211> LENGTH: 13
<212> TYPE: PRT
<213> ORGANISM: Influenza A virus

<400> SEQUENCE: 30

Pro Asn Ile Gly Asn Gln Arg Ala Leu Tyr Asn Thr Glu
1               5                   10

<210> SEQ ID NO 31
<211> LENGTH: 529
<212> TYPE: PRT
<213> ORGANISM: Influenza A virus

<400> SEQUENCE: 31

Met Lys Ala Ile Leu Leu Val Leu Leu Cys Ala Phe Ala Ala Thr Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Gly Gly Ile
        50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Val Ser Ser Trp Ser Tyr Ile
                85                  90                  95

Val Glu Thr Ser Asn Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Lys Phe Glu Ile Phe Pro Lys Thr Ser Ser Trp Pro Asn His Glu
        130                 135                 140

Thr Thr Arg Gly Val Thr Ala Ala Cys Pro Tyr Ala Gly Ala Ser Ser
145                 150                 155                 160

Phe Tyr Arg Asn Leu Leu Trp Leu Val Lys Lys Glu Asn Ser Tyr Pro
                165                 170                 175

Lys Leu Ser Lys Ser Tyr Val Asn Asn Lys Gly Lys Glu Val Leu Val

```
            180                 185                 190
Leu Trp Gly Val His His Pro Pro Thr Ser Thr Asp Gln Gln Ser Leu
            195                 200                 205

Tyr Gln Asn Ala Asp Ala Tyr Val Ser Val Gly Ser Ser Lys Tyr Asp
        210                 215                 220

Arg Arg Phe Thr Pro Glu Ile Ala Ala Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Val Ala Pro Arg Tyr Ala Phe
            260                 265                 270

Ala Leu Asn Arg Gly Ser Glu Ser Gly Ile Ile Thr Ser Asp Ala Pro
        275                 280                 285

Val His Asp Cys Asp Thr Lys Cys Gln Thr Pro His Gly Ala Ile Asn
290                 295                 300

Ser Ser Leu Pro Phe Gln Asn Ile His Pro Val Thr Ile Gly Glu Cys
305                 310                 315                 320

Pro Lys Tyr Val Lys Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Leu Ile Asp Gly Trp Tyr Gly Tyr
        355                 360                 365

His His Gln Asn Gly Gln Gly Ser Gly Tyr Ala Ala Asp Gln Lys Ser
        370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Val Val Gly Lys Glu Phe Asn Asn
                405                 410                 415

Leu Glu Arg Arg Ile Lys Asn Leu Asn Lys Lys Val Asp Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Ala Arg Ser Gln Leu Arg Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Met Val Tyr
        515                 520                 525

Gln

<210> SEQ ID NO 32
<211> LENGTH: 529
<212> TYPE: PRT
<213> ORGANISM: Influenza A virus

<400> SEQUENCE: 32

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
```

```
                    20                  25                  30
Val Asp Thr Val Leu Glu Lys Asn Val Thr Val Thr His Ser Val Asn
                35                  40                  45

Leu Leu Glu Asp Ser His Asn Gly Lys Leu Cys Lys Leu Lys Gly Ile
        50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
                100                 105                 110

Ile Asp Tyr Glu Glu Leu Arg Glu Gln Leu Ser Ser Val Ser Ser Phe
                115                 120                 125

Glu Lys Phe Glu Ile Phe Pro Lys Thr Ser Ser Trp Pro Asn His Glu
                130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
                180                 185                 190

Leu Trp Gly Val His His Pro Pro Thr Gly Thr Asp Gln Gln Ser Leu
                195                 200                 205

Tyr Gln Asn Ala Asp Ala Tyr Val Ser Val Gly Ser Ser Lys Tyr Asn
                210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
                260                 265                 270

Ala Leu Asn Arg Gly Ser Gly Ser Gly Ile Ile Thr Ser Asp Ala Pro
                275                 280                 285

Val His Asp Cys Asn Thr Lys Cys Gln Thr Pro His Gly Ala Ile Asn
                290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
                355                 360                 365

His His Gln Asn Glu Gln Gly Ser Gly Tyr Ala Ala Asp Gln Lys Ser
                370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445
```

```
Glu Arg Thr Leu Asp Phe His Asp Ser Asn Val Arg Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
            485                 490                 495

Arg Asn Gly Thr Tyr Asp Tyr Pro Lys Tyr Ser Glu Glu Ser Lys Leu
        500                 505                 510

Asn Arg Glu Glu Ile Asp Gly Val Lys Leu Glu Ser Met Gly Val Tyr
    515                 520                 525

Gln
```

<210> SEQ ID NO 33
<211> LENGTH: 529
<212> TYPE: PRT
<213> ORGANISM: Influenza A virus

<400> SEQUENCE: 33

```
Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Glu Arg Ser Trp Ser Tyr Ile
                85                  90                  95

Val Glu Ile Pro Asn Ser Glu Asn Gly Thr Cys Tyr Pro Gly Asp Phe
            100                 105                 110

Thr Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Asn
130                 135                 140

Thr Ala Arg Gly Val Thr Ala Ala Cys Ser His Ala Gly Lys Ser Ser
145                 150                 155                 160

Phe Tyr Arg Asn Leu Leu Trp Leu Thr Glu Lys Asp Gly Ser Tyr Pro
                165                 170                 175

Asn Leu Lys Asn Ser Tyr Val Asn Lys Lys Gly Lys Glu Val Leu Val
            180                 185                 190

Leu Trp Gly Val His His Pro Ser Ser Ile Lys Glu Gln Gln Thr Leu
        195                 200                 205

Tyr Gln Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Asn Gly Asn Leu Ile Ala Pro Trp Tyr Ala Phe
            260                 265                 270

Ala Leu Ser Arg Gly Phe Glu Ser Gly Ile Ile Thr Ser Asn Ala Ser
        275                 280                 285
```

```
Met His Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Lys Arg Met Glu Asn Leu Asn Lys Lys Val Asp Asp Gly Phe
                420                 425                 430

Leu Asp Ile Trp Thr Tyr Asn Ala Glu Leu Leu Ile Leu Leu Glu Asn
            435                 440                 445

Glu Arg Thr Leu Asp Phe His Asp Ser Asn Val Lys Asn Leu Tyr Glu
    450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
                500                 505                 510

Asn Arg Glu Lys Ile Asp Gly Val Lys Leu Glu Ser Met Gly Val Tyr
            515                 520                 525

Gln

<210> SEQ ID NO 34
<211> LENGTH: 535
<212> TYPE: PRT
<213> ORGANISM: Influenza A virus

<400> SEQUENCE: 34

Lys Ile Lys Lys Thr Lys Met Lys Ala Lys Leu Leu Val Leu Leu Cys
1               5                   10                  15

Ala Leu Ser Ala Thr Asp Ala Asp Thr Ile Cys Ile Gly Tyr His Ala
                20                  25                  30

Asn Asn Ser Thr Asp Thr Val Asp Thr Val Leu Glu Lys Asn Val Thr
            35                  40                  45

Val Thr His Ser Val Asn Leu Leu Glu Asp Ser His Asn Gly Lys Leu
        50                  55                  60

Cys Arg Leu Lys Gly Ile Ala Pro Leu Gln Leu Gly Lys Cys Asn Ile
65                  70                  75                  80

Ala Gly Trp Ile Leu Gly Asn Pro Glu Cys Glu Ser Leu Val Thr Lys
                85                  90                  95

Lys Ser Trp Ser Tyr Ile Ala Glu Thr Pro Asn Ser Glu Asn Gly Thr
                100                 105                 110

Cys Tyr Pro Gly Tyr Phe Ala Asp Tyr Glu Glu Leu Arg Glu Gln Leu
            115                 120                 125
```

```
Ser Ser Val Ser Ser Phe Glu Arg Phe Glu Ile Phe Pro Lys Glu Arg
        130                 135                 140

Ser Trp Pro Lys His Asn Val Thr Arg Gly Val Thr Ala Ser Cys Ser
145                 150                 155                 160

His Lys Gly Lys Ser Ser Phe Tyr Arg Asn Leu Leu Trp Leu Thr Glu
                165                 170                 175

Lys Asn Gly Ser Tyr Pro Asn Leu Ser Lys Ser Tyr Val Asn Asn Lys
            180                 185                 190

Glu Lys Glu Val Leu Val Leu Trp Gly Val His His Pro Ser Asn Ile
        195                 200                 205

Glu Asp Gln Lys Thr Ile Tyr Arg Lys Glu Asn Ala Tyr Val Ser Val
    210                 215                 220

Val Ser Ser Asn Tyr Asn Arg Arg Phe Thr Pro Glu Ile Ala Glu Arg
225                 230                 235                 240

Pro Lys Val Arg Gly Gln Ala Gly Arg Ile Asn Tyr Tyr Trp Thr Leu
                245                 250                 255

Leu Glu Pro Gly Asp Thr Ile Thr Phe Glu Ala Asn Gly Asn Leu Ile
            260                 265                 270

Ala Pro Trp His Ala Phe Ala Leu Asn Arg Gly Ser Gly Ser Gly Ile
        275                 280                 285

Ile Thr Ser Asn Ala Ser Met Asp Glu Cys Asp Thr Lys Cys Gln Thr
    290                 295                 300

Pro Gln Gly Ala Ile Asn Ser Ser Leu Pro Phe Gln Asn Ile His Pro
305                 310                 315                 320

Val Thr Ile Gly Glu Cys Pro Lys Tyr Val Arg Ser Thr Lys Leu Arg
                325                 330                 335

Met Val Thr Gly Leu Arg Asn Ile Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asp Gly Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn Lys Leu Glu Lys Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asn Asn
                485                 490                 495

Glu Cys Met Glu Ser Val Lys Asn Gly Thr Tyr Asp Tyr Pro Lys Tyr
            500                 505                 510

Ser Glu Glu Ser Lys Leu Asn Arg Glu Lys Ile Asp Gly Val Lys Leu
        515                 520                 525

Glu Ser Met Gly Val Tyr Gln
    530                 535
```

<210> SEQ ID NO 35
<211> LENGTH: 561
<212> TYPE: PRT
<213> ORGANISM: Influenza A virus

<400> SEQUENCE: 35

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Arg Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
370                 375                 380
```

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
            405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
            485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
            515                 520                 525

Gln Ser Thr Val Ala Ser Ser Leu Val Leu Val Val Ser Leu Gly Ala
            530                 535                 540

Ile Ser Phe Trp Met Cys Ser Asn Gly Ser Leu Gln Cys Arg Ile Cys
545                 550                 555                 560

Ile

<210> SEQ ID NO 36
<211> LENGTH: 120
<212> TYPE: PRT
<213> ORGANISM: Influenza A virus

<400> SEQUENCE: 36

Tyr Glu Glu Leu Arg Glu Gln Leu Ser Ser Val Ser Ser Phe Glu Lys
1               5                   10                  15

Phe Glu Ile Phe Pro Lys Thr Ser Ser Trp Pro Asn His Glu Thr Thr
                20                  25                  30

Arg Gly Val Thr Ala Ala Cys Pro Tyr Ala Gly Ala Ser Ser Phe Tyr
            35                  40                  45

Arg Asn Leu Leu Trp Leu Val Lys Lys Glu Asn Ser Tyr Pro Lys Leu
    50                  55                  60

Ser Lys Ser Tyr Val Asn Asn Lys Gly Lys Glu Val Leu Val Leu Trp
65                  70                  75                  80

Gly Val His His Pro Pro Thr Ser Thr Asp Gln Gln Ser Leu Tyr Gln
                85                  90                  95

Asn Ala Asp Ala Tyr Val Ser Val Gly Ser Ser Lys Tyr Asp Arg Arg
            100                 105                 110

Phe Thr Pro Glu Ile Ala Ala Arg
            115                 120

<210> SEQ ID NO 37
<211> LENGTH: 120
<212> TYPE: PRT
<213> ORGANISM: Influenza A virus

<400> SEQUENCE: 37

Tyr Glu Glu Leu Arg Glu Gln Leu Ser Ser Val Ser Ser Phe Glu Lys
1 5 10 15

```
Phe Glu Ile Phe Pro Lys Thr Ser Ser Trp Pro Asn His Glu Thr Thr
             20                  25                  30

Lys Gly Val Thr Ala Ala Cys Ser Tyr Ala Gly Ala Ser Ser Phe Tyr
         35                  40                  45

Arg Asn Leu Leu Trp Leu Thr Lys Lys Gly Ser Ser Tyr Pro Lys Leu
     50                  55                  60

Ser Lys Ser Tyr Val Asn Asn Lys Gly Lys Glu Val Leu Val Leu Trp
 65                  70                  75                  80

Gly Val His His Pro Pro Thr Gly Thr Asp Gln Gln Ser Leu Tyr Gln
                 85                  90                  95

Asn Ala Asp Ala Tyr Val Ser Val Gly Ser Ser Lys Tyr Asn Arg Arg
                100                 105                 110

Phe Thr Pro Glu Ile Ala Ala Arg
            115                 120

<210> SEQ ID NO 38
<211> LENGTH: 120
<212> TYPE: PRT
<213> ORGANISM: Influenza A virus

<400> SEQUENCE: 38

Tyr Glu Glu Leu Arg Glu Gln Leu Ser Ser Val Ser Ser Phe Glu Arg
 1               5                  10                  15

Phe Glu Ile Phe Pro Lys Glu Ser Ser Trp Pro Lys His Asn Thr Ala
             20                  25                  30

Arg Gly Val Thr Ala Ala Cys Ser His Ala Gly Lys Ser Ser Phe Tyr
         35                  40                  45

Arg Asn Leu Leu Trp Leu Thr Glu Lys Asp Gly Ser Tyr Pro Asn Leu
     50                  55                  60

Lys Asn Ser Tyr Val Asn Lys Lys Gly Lys Glu Val Leu Val Leu Trp
 65                  70                  75                  80

Gly Val His His Pro Ser Ser Ile Lys Glu Gln Gln Thr Leu Tyr Gln
                 85                  90                  95

Lys Glu Asn Ala Tyr Val Ser Val Val Ser Ser Asn Tyr Asn Arg Arg
                100                 105                 110

Phe Thr Pro Glu Ile Ala Glu Arg
            115                 120

<210> SEQ ID NO 39
<211> LENGTH: 120
<212> TYPE: PRT
<213> ORGANISM: Influenza A virus

<400> SEQUENCE: 39

Tyr Glu Glu Leu Arg Glu Gln Leu Ser Ser Val Ser Ser Phe Glu Arg
 1               5                  10                  15

Phe Glu Ile Phe Pro Lys Glu Arg Ser Trp Pro Lys His Asn Val Thr
             20                  25                  30

Arg Gly Val Thr Ala Ser Cys Ser His Lys Gly Lys Ser Ser Phe Tyr
         35                  40                  45

Arg Asn Leu Leu Trp Leu Thr Glu Lys Asn Gly Ser Tyr Pro Asn Leu
     50                  55                  60

Ser Lys Ser Tyr Val Asn Asn Lys Glu Lys Glu Val Leu Val Leu Trp
 65                  70                  75                  80

Gly Val His His Pro Ser Asn Ile Glu Asp Gln Lys Thr Leu Tyr Arg
                 85                  90                  95
```

```
Lys Glu Asn Ala Tyr Val Ser Val Val Ser Ser Asn Tyr Asn Arg Arg
            100                 105                 110

Phe Thr Pro Glu Ile Ala Glu Arg
        115                 120

<210> SEQ ID NO 40
<211> LENGTH: 120
<212> TYPE: PRT
<213> ORGANISM: Influenza A virus

<400> SEQUENCE: 40

Tyr Glu Glu Leu Arg Glu Gln Leu Ser Ser Val Ser Ser Phe Glu Arg
1               5                   10                  15

Phe Glu Ile Phe Pro Lys Thr Ser Ser Trp Pro Asn His Asp Ser Asn
            20                  25                  30

Lys Gly Val Thr Ala Ala Cys Pro His Ala Gly Ala Lys Ser Phe Tyr
        35                  40                  45

Lys Asn Leu Ile Trp Leu Val Lys Lys Gly Asn Ser Tyr Pro Lys Leu
    50                  55                  60

Ser Lys Ser Tyr Ile Asn Asp Lys Gly Lys Glu Val Leu Val Leu Trp
65                  70                  75                  80

Gly Ile His His Pro Ser Thr Ser Ala Asp Gln Gln Ser Leu Tyr Gln
                85                  90                  95

Asn Ala Asp Thr Tyr Val Phe Val Gly Ser Ser Arg Tyr Ser Lys Lys
            100                 105                 110

Phe Lys Pro Glu Ile Ala Ile Arg
        115                 120

<210> SEQ ID NO 41
<211> LENGTH: 125
<212> TYPE: PRT
<213> ORGANISM: Influenza A virus

<400> SEQUENCE: 41

Glu Val Gln Leu Val Gln Ser Gly Gly Gly Val Val Gln Pro Arg Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Arg Asn Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ser Val Tyr Tyr Cys
                85                  90                  95

Ala Arg Glu Leu Leu Met Asp Tyr Tyr Asp His Ile Gly Tyr Ser Pro
            100                 105                 110

Gly Pro Thr Trp Gly Gln Gly Thr Leu Val Thr Val Ser
        115                 120                 125

<210> SEQ ID NO 42
<211> LENGTH: 126
<212> TYPE: PRT
<213> ORGANISM: Influenza A virus

<400> SEQUENCE: 42

Glu Val Gln Leu Val Glu Ser Gly Gly Gly Val Val Gln Pro Gly Gly
```

1 5 10 15

Ser Leu Arg Leu Ser Cys Ile Ala Ser Ala Phe Asn Leu Gly Ile Phe
20 25 30

Gly Met His Trp Val Arg Gln Ala Pro Gly Lys Gly Leu Glu Trp Val
35 40 45

Ala Phe Ile Arg Tyr Asp Gly Gly Lys Thr Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Thr Glu Asp Thr Ala Leu Tyr Tyr Cys
85 90 95

Ala Arg Asp Ala Thr Ala Asp Tyr Tyr Gly Pro Gly Ser Tyr Pro Asn
100 105 110

Trp Leu Asp Pro Trp Gly Gln Gly Thr Leu Val Thr Val Ser
115 120 125

<210> SEQ ID NO 43
<211> LENGTH: 127
<212> TYPE: PRT
<213> ORGANISM: Influenza A virus

<400> SEQUENCE: 43

Glu Val Gln Leu Val Gln Ser Gly Gly Ala Val Val Gln Pro Gly Arg
1 5 10 15

Ser Leu Arg Leu Ser Cys Ala Ala Ser Gly Phe Thr Phe Ser Ile Tyr
20 25 30

Ala Met His Trp Val Arg Gln Thr Pro Gly Lys Gly Leu Glu Trp Val
35 40 45

Ala Leu Ile Ser Tyr Asp Gly Asn Asn Lys Tyr Tyr Ala Asp Ser Val
50 55 60

Lys Gly Arg Phe Thr Ile Ser Arg Asp Asn Tyr Lys Asn Thr Leu Tyr
65 70 75 80

Leu Gln Met Lys Gly Leu Arg Ala Glu Asp Thr Ala Leu Tyr Tyr Cys
85 90 95

Ala Arg Arg Ile Thr Glu Lys Gly Tyr Tyr Asn Asp Ser Gly Arg Pro
100 105 110

Asn Trp Phe Asp Pro Trp Gly Gln Gly Thr Leu Val Thr Val Ser
115 120 125

<210> SEQ ID NO 44
<211> LENGTH: 128
<212> TYPE: PRT
<213> ORGANISM: Influenza A virus

<400> SEQUENCE: 44

Arg Gly Gln Leu Val Gln Ser Gly Gly Gly Val Val Gln Pro Gly Arg
1 5 10 15

Ser Leu Arg Leu Ser Cys Ala Ala Ser Gly Phe Val Phe Asn Val Phe
20 25 30

Ala Ile His Trp Val Arg Gln Ala Pro Gly Lys Gly Leu Glu Trp Leu
35 40 45

Ala Thr Ile Ser Tyr Asp Gly Leu Asn Lys Tyr Tyr Ala Asp Ser Val
50 55 60

Lys Gly Arg Ile Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys

-continued

```
                85                  90                  95
Val Arg Asp Ser Glu Glu Ser Thr Tyr Tyr Gly Asp Thr Met Trp Val
                100                 105                 110

Tyr Asn Trp Phe Asp Leu Trp Gly Gln Gly Thr Leu Val Thr Val Ser
                115                 120                 125

<210> SEQ ID NO 45
<211> LENGTH: 232
<212> TYPE: PRT
<213> ORGANISM: Influenza A virus

<400> SEQUENCE: 45

Lys Leu Arg Gly Val Ala Pro Leu His Leu Gly Lys Cys Asn Ile Ala
1               5                   10                  15

Gly Trp Ile Leu Gly Asn Pro Glu Cys Glu Ser Leu Ser Thr Ala Ser
                20                  25                  30

Ser Trp Ser Tyr Ile Val Glu Thr Pro Ser Ser Asp Asn Gly Thr Cys
            35                  40                  45

Tyr Pro Gly Asp Phe Ile Asp Tyr Glu Glu Leu Arg Glu Gln Leu Ser
        50                  55                  60

Ser Val Ser Ser Phe Glu Arg Phe Glu Ile Phe Pro Lys Thr Ser Ser
65                  70                  75                  80

Trp Pro Asn His Asp Ser Asn Lys Gly Val Thr Ala Ala Cys Pro His
                85                  90                  95

Ala Gly Ala Lys Ser Phe Tyr Lys Asn Leu Ile Trp Leu Val Lys Lys
                100                 105                 110

Gly Asn Ser Tyr Pro Lys Leu Ser Lys Ser Tyr Ile Asn Asp Lys Gly
                115                 120                 125

Lys Glu Val Leu Val Leu Trp Gly Ile His His Pro Ser Thr Ser Ala
            130                 135                 140

Asp Gln Gln Ser Leu Tyr Gln Asn Ala Asp Thr Tyr Val Phe Val Gly
145                 150                 155                 160

Ser Ser Arg Tyr Ser Lys Lys Phe Lys Pro Glu Ile Ala Ile Arg Pro
                165                 170                 175

Lys Val Arg Asp Gln Glu Gly Arg Met Asn Tyr Tyr Trp Thr Leu Val
                180                 185                 190

Glu Pro Gly Asp Lys Ile Thr Phe Glu Ala Thr Gly Asn Leu Val Val
                195                 200                 205

Pro Arg Tyr Ala Phe Ala Met Glu Arg Asn Ala Gly Ser Gly Ile Thr
            210                 215                 220

Ile Ser Asp Thr Pro Val His Asp
225                 230

<210> SEQ ID NO 46
<211> LENGTH: 232
<212> TYPE: PRT
<213> ORGANISM: Influenza A virus

<400> SEQUENCE: 46

Lys Leu Lys Gly Ile Ala Pro Leu Gln Leu Gly Lys Cys Asn Ile Ala
1               5                   10                  15

Gly Trp Leu Leu Gly Asn Pro Glu Cys Asp Leu Leu Leu Thr Ala Ser
                20                  25                  30

Ser Trp Ser Tyr Ile Val Glu Thr Ser Asn Ser Lys Asn Gly Thr Cys
            35                  40                  45

Tyr Pro Gly Asp Phe Ile Asp Tyr Glu Glu Leu Arg Glu Gln Leu Ser
```

```
               50                  55                  60
Ser Val Ser Ser Phe Glu Arg Phe Glu Ile Phe Pro Lys Thr Ser Ser
 65                  70                  75                  80

Trp Pro Asn His Glu Thr Thr Lys Gly Val Thr Ala Ala Cys Ser Tyr
                 85                  90                  95

Ala Gly Ala Ser Ser Phe Tyr Arg Asn Leu Leu Trp Leu Thr Lys Lys
            100                 105                 110

Gly Ser Ser Tyr Pro Lys Leu Ser Lys Ser Tyr Val Asn Asn Lys Gly
        115                 120                 125

Lys Glu Val Leu Val Leu Trp Gly Val His His Pro Pro Thr Gly Thr
    130                 135                 140

Asp Gln Gln Ser Leu Tyr Gln Asn Ala Asp Ala Tyr Val Ser Val Gly
145                 150                 155                 160

Ser Ser Lys Tyr Asn Arg Arg Phe Thr Pro Glu Ile Ala Ala Arg Pro
                165                 170                 175

Lys Val Arg Asp Gln Ala Gly Arg Met Asn Tyr Tyr Trp Thr Leu Leu
            180                 185                 190

Glu Pro Gly Asp Thr Ile Thr Phe Glu Ala Thr Gly Asn Leu Ile Ala
        195                 200                 205

Pro Trp Tyr Ala Phe Ala Leu Asn Arg Gly Ser Gly Ser Gly Ile Thr
    210                 215                 220

Ile Ser Asp Ala Pro Val His Asp
225                 230

<210> SEQ ID NO 47
<211> LENGTH: 231
<212> TYPE: PRT
<213> ORGANISM: Influenza A virus

<400> SEQUENCE: 47

Arg Leu Lys Gly Ile Ala Pro Leu Gln Leu Gly Lys Cys Asn Ile Ala
  1               5                  10                  15

Gly Trp Leu Leu Gly Asn Pro Glu Cys Asp Pro Leu Ser Pro Val Arg
             20                  25                  30

Ser Trp Ser Tyr Ile Val Glu Thr Pro Asn Ser Glu Asn Gly Thr Cys
         35                  40                  45

Tyr Pro Gly Asp Phe Ile Asp Tyr Glu Glu Leu Arg Glu Gln Leu Ser
     50                  55                  60

Ser Val Ser Ser Phe Glu Arg Phe Glu Ile Phe Pro Lys Thr Ser Ser
 65                  70                  75                  80

Trp Pro Asn His Asn Thr Asn Gly Val Thr Ala Ala Cys Ser His Glu
                 85                  90                  95

Gly Lys Ser Ser Phe Tyr Arg Asn Leu Leu Trp Leu Thr Glu Lys Glu
            100                 105                 110

Gly Ser Tyr Pro Lys Leu Lys Asn Ser Tyr Val Asn Lys Lys Gly Lys
        115                 120                 125

Glu Val Leu Val Leu Trp Gly Ile His His Pro Asn Ser Lys Glu
    130                 135                 140

Gln Gln Asn Leu Tyr Gln Asn Glu Asn Ala Tyr Val Ser Val Val Thr
145                 150                 155                 160

Ser Asn Tyr Asn Arg Arg Phe Thr Pro Glu Ile Ala Glu Arg Pro Lys
                165                 170                 175

Val Arg Asp Gln Ala Gly Arg Met Asn Tyr Tyr Trp Thr Leu Leu Glu
            180                 185                 190
```

```
Pro Gly Asp Thr Ile Thr Phe Glu Ala Asn Gly Asn Leu Ile Ala Pro
            195                 200                 205

Arg Tyr Ala Phe Ala Leu Ser Arg Gly Phe Gly Ser Gly Ile Thr Ile
    210                 215                 220

Ser Asn Ala Ser Met His Glu
225             230

<210> SEQ ID NO 48
<211> LENGTH: 231
<212> TYPE: PRT
<213> ORGANISM: Influenza A virus

<400> SEQUENCE: 48

Leu Leu Lys Gly Ile Ala Pro Leu Gln Leu Gly Asn Cys Ser Val Ala
1               5                   10                  15

Gly Trp Leu Leu Gly Asn Pro Glu Cys Glu Leu Leu Ile Ser Lys Glu
            20                  25                  30

Ser Trp Ser Tyr Ile Val Glu Lys Pro Asn Pro Glu Asn Gly Thr Cys
        35                  40                  45

Tyr Pro Gly His Phe Ala Asp Tyr Glu Glu Leu Arg Glu Gln Leu Ser
    50                  55                  60

Ser Val Ser Ser Phe Glu Arg Phe Glu Ile Phe Pro Lys Glu Ser Ser
65                  70                  75                  80

Trp Pro Asn His Thr Val Thr Gly Val Ser Ala Ser Cys Ser His Asn
                85                  90                  95

Gly Glu Ser Ser Phe Tyr Arg Asn Leu Leu Trp Leu Thr Gly Lys Asn
            100                 105                 110

Gly Leu Tyr Pro Lys Leu Ser Lys Ser Tyr Ala Asn Asn Lys Glu Lys
        115                 120                 125

Glu Val Leu Val Leu Trp Gly Val His His Pro Asn Ile Gly Asp
    130                 135                 140

Gln Lys Ala Leu Tyr His Thr Phe Asn Ala Tyr Val Ser Val Val Ser
145                 150                 155                 160

Ser His Tyr Ser Arg Lys Phe Thr Pro Glu Ile Ala Lys Arg Pro Lys
                165                 170                 175

Val Arg Asp Gln Glu Gly Arg Ile Asn Tyr Tyr Trp Thr Leu Leu Glu
            180                 185                 190

Pro Gly Asp Thr Ile Thr Phe Glu Ala Asn Gly Asn Leu Ile Ala Pro
            195                 200                 205

Arg Tyr Ala Phe Ala Leu Ser Arg Gly Phe Gly Ser Gly Ile Thr Asn
    210                 215                 220

Ser Asn Ala Pro Met Asp Lys
225             230
```